US010119487B1

(12) United States Patent
Skiles et al.

(10) Patent No.: US 10,119,487 B1
(45) Date of Patent: Nov. 6, 2018

(54) CONTROL PANEL FOR ENERGY EFFICIENT OPERATIONS OF VEHICLE WARMERS

(71) Applicants: Harvey Martin, Frankfort, IN (US); Kurt Scheppers, Carmel, IN (US)

(72) Inventors: Cammy L. Skiles, Rossville, IN (US); Karen L. Skiles, Rossville, IN (US); Harvey Martin, Frankfort, IN (US)

( * ) Notice: Subject to any disclaimer, the term of this patent is extended or adjusted under 35 U.S.C. 154(b) by 0 days.

(21) Appl. No.: 15/694,747

(22) Filed: Sep. 1, 2017

Related U.S. Application Data

(60) Provisional application No. 62/382,610, filed on Sep. 1, 2016.

(51) Int. Cl.
*F02D 41/06* (2006.01)
*F02N 19/10* (2010.01)
(52) U.S. Cl.
CPC ......... *F02D 41/064* (2013.01); *F02D 41/068* (2013.01); *F02N 19/10* (2013.01)
(58) Field of Classification Search
CPC ...... F02D 41/06; F02D 41/064; F02D 41/068; F02N 19/10
See application file for complete search history.

(56) References Cited

U.S. PATENT DOCUMENTS

| 7,036,746 | B2* | 5/2006 | Murgu | B60H 1/2209 165/41 |
| 2009/0320805 | A1* | 12/2009 | Lang | F02M 25/0854 123/518 |
| 2012/0163781 | A1* | 6/2012 | Sedlacek | F24H 1/102 392/471 |

* cited by examiner

*Primary Examiner* — Hieu T Vo
(74) *Attorney, Agent, or Firm* — E. Victor Indiano; Indiano & McConnell, LLC

(57) ABSTRACT

A vehicle fluid heating system is provided for achieving an elevated pre-determined fluid temperature for at least one fluid of a first and second vehicle during an idle period having a duration defined by a start point and an end point. The heating system includes a first vehicle fluid heater that is configured for being coupled to the first vehicle in thermal communication with the first fluid of the first vehicle. A second vehicle fluid heater is provided that is configured for being coupled to the second vehicle in thermal communication with the first fluid of the second vehicle. At least one temperature sensor is provided for sensing a temperature of a temperature source that has a correlative relationship to the first fluid of the first and second vehicles. A settable timer is provided for enabling the user to establish a start point and an end point of the idle period of the first and second vehicles. A controller is in communication with an electrical source for controlling the flow of electricity from the electrical source to the first and second vehicle fluid heaters.

19 Claims, 20 Drawing Sheets

CONTROL PANEL FOR ENERGY EFFICIENT OPERATIONS OF VEHICLE WARMERS

PRIORITY CLAIM

This non-provisional patent application claims benefit of priority to Skiles et al U.S. Provisional Patent Application Nos. 62/382,610 filed 1 Sep. 2016 for CONTROL PANEL FOR ENERGY EFFICIENT OPERATIONS OF VEHICLE WARMERS which is fully incorporated herein by reference.

TECHNICAL FIELD OF THE INVENTION

The present invention relates to vehicle maintenance devices, and more particularly, to a control panel that is capable of controlling the flow of electricity to a vehicle heater such as an engine block heater used to heat vehicles during the cold weather to promote starting and operation of the vehicle.

BACKGROUND OF THE INVENTION

Cold weather makes it more difficult to start vehicles, and especially commercial vehicles, and most especially commercial vehicles with diesel engines. Several factors contribute to this difficulty of starting.

One factor is the strength of the battery. As battery amperage output is a function of temperature, lower temperatures result in lower battery amperage, which gives the battery less power to turn the engine. This loss of amperage in a battery in cold weather can be substantial. For example, it is not unusual for a battery to lose 35% of its power at 37° F., and as much as 60% of its power at 0° F. The second factor relates to oil viscosity. As the viscosity of an oil tends to increase at decreasing temperatures, the oil within the engine at colder temperatures presents greater resistance to the rotation of the engine than a more free-flowing less viscous oil does at warmer temperatures. In summary, cold weather forces a lower powered battery to overcome increased turning resistance caused by thicker, more viscous oil.

In order to counteract these difficulties, it is quite common to employ a block heater with a commercial vehicle (and even with consumer vehicles in very cold areas such as Alaska. A block heater comprises a probe-like resistive heater that is insertable into an engine component, so that the probe extends into the interior of the engine block, and preferably, into an oil reservoir within the engine.

Many commercial vehicles are fitted with a plug having a removable cap for insertion of the probe. When the cap is removed, the probe can be inserted into the block, so that the heated end of the probe extends directly into the oil within the block, to keep the oil warm.

In addition to the probe described above, other types of engine block heaters exist. For example, there exists dip stick type probes that can be inserted into the oil fill tube where the dip stick normally resides. Another alternative is to employ a resistive heater probe that is placed into the coolant reservoir of the vehicle, rather than the oil reservoir of the vehicle. Additionally, resistive probes can be placed in a fuel reservoir of a vehicle, such as a gas tank, since heavier fuels, such as diesel fuel have a tendency to become gel-like at very low temperatures.

Heater probes of the type described above typically come in two primary varieties—permanent and removable. In this regard, many vehicles come equipped with heater probes that are permanently installed in the vehicle. At night, one connects a plug to an outlet on the heater block, to thereby connect the source of electricity to the heater probe. In other situations, a removable heater probe is used, such as the dipstick heater probe. In such cases, the heater probe and plug are connected to the block and unconnected to the block every time that the device is being used.

Heater probes of the type described above can be used either singly or in combination. For example, some facilities provide a first heater that is insertable into the oil reservoir, and a second heater that is insertable into the coolant reservoir. Some facilities will even employ three probes, with the third probe being disposed within the gas tank of the vehicle to keep the fuel from becoming gel-like.

The extent to which a company will employ probes to keep its vehicles warm is largely dependent upon the type of vehicles that are employed by the company, and the nature of the climate in which the vehicles operate. Clearly, a company operating a fleet of diesel powered delivery vehicles in Manitoba would likely employ a more extensive array of vehicle heating devices than a company operating a fleet of gas powered vehicles in a relatively warmer southern area such as Kentucky or Tennessee.

Typically, a fleet operator will couple these heaters through a cord to a plug that is disposed on the wall of the garage in which the vehicle is kept, or may be placed on an electricity station within the parking lot or parking area in which the vehicle is placed. A typical procedure for employing the engine heaters is to insert the heaters into their appropriate reservoir (coolant, oil, fuel) when the vehicle is parked at the end of its shift, and to allow the heater to operate during the time that the vehicle is parked, until such time as the vehicle is ready for use on its next shift. At such time, the heaters will be disconnected from the source of electricity, and the vehicle will be driven away.

Most known vehicle heaters in use today are equipped with controls that comprise little more than an on-off functionality. Usually, the act of connecting the heater to a source of electricity, such as by plugging it in, causes the heater to actuate and begin its operation. Similarly, the outlets that are typically used in connection with such vehicle heaters operate similarly to other conventional outlets, as they are normally defaulted to be in a "on position", wherein they can provide current to any device that is plugged into the outlet. Many such outlets include a switch for controlling the flow of electricity to the outlet that can take the form of a localized switch that is dedicated to the outlet, or else a circuit breaker type switch that may control a plurality of outlets.

In commercial operations, the most typical setup is to employ a single circuit breaker that controls a single outlet. This single breaker-single outlet arrangement is used because a typical vehicle heater such as a block heater, fluid coolant heater or fuel heater will often draw about 1300 watts of power. Because of this high-power draw, it has been found that a single circuit breaker should generally not be used to control the operation of more than one outlet.

Although the devices described above perform their function in a workmanlike manner, room for improvement exists. As described above, the vehicle heater for a commercial vehicle draws a significant amount of power that results in significant costs for the electricity used to power the heater. As such, it would be desirable to provide a heater that provides a more efficient operation, and draws less electricity than the heaters described above. By drawing less electricity, a "smarter" system would have the potential to save the fleet operators significant amounts of money due to the reduced energy consumption.

The following example illustrates the lack of efficiency in the current systems. In school bus operations, the busses are typically started and begin their morning routes somewhere around 6:00 a.m. These morning routes are often finished by 9:00 a.m. or 10:00 a.m. After the morning routes are finished, the busses then sit idle in their parking areas from about 10:00 a.m. to about 2:00 p.m. when the afternoon routes begin. The afternoon routes typically keep the buses engaged between 2:00 p.m. and 5:00 p.m. or 6:00 p.m. At 6:00 p.m., the buses return back to their parking areas and are parked overnight with the engines shut off until the next morning at 6:00 a.m., when they are again restarted. Additionally, some buses may be operated into the evening hours, such as those buses that are used for transporting students to special events, such as sporting events.

In the scenario set forth above, the school bus driver typically connects his vehicle to the block heater during the day time non-use frame between the morning and afternoon bus routes (approximately 10:00 a.m. to 2:00 p.m.) and then again during the evening, non-use time frame between the end of the evening routes and the beginning of the next morning routes which lasts between approximately 6:00 p.m. and 6:00 a.m.

In the scenario given above, the heater would be drawing current at a fairly substantial rate for a 16-hour period each day. This 16-hour period is not significantly different from the operation of a commercial fleet, where the trucks are operated on a single shift. In such cases, the trucks would generally be operated between about 8:00 a.m. and 6:00 p.m. and connected to a heater block between 6:00 p.m. and 8:00 a.m. the next day. However, a primary difference between the operation of a school bus fleet and a commercial vehicle fleet is that a school bus fleet will have two idle (non-use) periods, with the first being between the morning and afternoon routes, and the second being overnight, whereas a commercial operation will have only a single idle time.

Although the above-described schedules are likely to apply to most of the vehicles within a respective school bus or commercial vehicle fleet, exceptions apply. As discussed above, some school buses are used in the evening for after school or evening events. Similarly, some of the commercial vehicles may be used at times other than the standard day shirt, or may be used for more than one shift during a day. As such, it would be beneficial to have some individual control over the electricity provided to individual vehicles, to enable the operator to accommodate vehicles having different schedules and different requirements.

One object of the present invention is to provide a device that is capable of efficiently controlling the operation of a vehicle maintenance device, such as a block heater for a vehicle, and especially a commercial vehicle.

SUMMARY OF THE INVENTION

In accordance with the present invention, a vehicle fluid heating system is provided for achieving an elevated predetermined fluid temperature for at least one fluid of a first and second vehicle during an idle period having a duration defined by a start point and an end point. The heating system comprises a first vehicle fluid heater that is configured for being coupled to the first vehicle in thermal communication with the first fluid of the first vehicle. A second vehicle fluid heater is provided that is configured for being coupled to the second vehicle in thermos communication with the first fluid of the second vehicle.

At least one temperature sensor is provided for sensing a temperature of a temperature source that has a correlative relationship to the first fluid of the first and second vehicles. A settable timer is provided for enabling the user to establish a start point and an end point of the idle period of the first and second vehicles. A controller is provided that is in communication with an electrical source for controlling the flow of electricity from the electrical source to the first and second vehicle fluid heaters. The controller is also in communication with the temperature sensor for receiving temperature information, and is in communication with the sellable timer for obtaining information about the start point and the end point of the vehicle idle periods. The controller includes a processor for receiving the temperature information, the idle period start points information and the idle point end information for determining a vehicle heating fluid interval having a duration less than the duration of the idle period that achieves an elevated, pore-determined fluid temperature as the end of the idle period. A switch actuator is provided for allowing the flow of electricity from the electrical source to the first and second fluid heaters during the fluid heating intervals.

In a preferred embodiment of the present invention, the device also includes an input device for enabling the user to input operational data into the controller, such as the idle period start point, along with the desired elevated predetermined fluid temperature.

The timer can include a calendar function for enabling the user to use the input device to input operational data for at least a first day having a first idle period start and end points, and a second day having a second idle period start and end points different from the start point and end point of the first day. This feature has the advantage of making the device flexible, and energy efficient, by enabling the user to program different start points and end points on days when the vehicle is likely to be used (such as week days and work days), and also on days when the vehicle is not likely to be used (weekends and non-work days).

The vehicle fluid heater preferably comprises a probe, that is placeable in the vehicle to directly contact the fluid within the vehicle. In a most preferred embodiment, the heater probe may also include a temperature sensor, for sensing the temperature of the fluid within the fluid reservoir being heated by the heater probe.

In a most preferred embodiment, the first and second vehicles may comprise first and second vehicle groups or zones, with each of the first and second vehicle groups comprising a plurality of vehicles, each with their own fluid heater. The controller is preferably configured to be able to independently and separably control the first and second vehicles or first and second vehicle groups. In another preferred embodiment, each particular vehicle includes more than one vehicle heater, such as an oil heater, coolant heater, and/or fuel heater. The controller would be configured to control the operation of each of these different heaters within the vehicle.

One feature of the present invention is that it permits the device to apply heat only intermittently, thus reducing the amount of time that the vehicle heating devices are actuated, and thereby reducing the electricity consumed by the vehicle heaters.

Preferably, a Below-Turn-On set point and an Above-Turn-Offset point are used. The Below-Turn-On set point is the temperature that must be reached (e.g. 25 degrees F.) before the device will turn on the heaters. The Above-Turn-Off set point is the temperature (e.g. 32 degrees F.) that, if reached, will cause the device to shut off the flow of electricity and heat to the vehicles. This use of set points has two important features. First, by establishing a set point, the devices can be controlled by the controller to not operate unless the ambient temperatures falls below the Below-Turn-On set point. Conversely, the Above-Turn-Off set point can represent the maximum temperature to which the vehicle fluids are heated by the devices, such that if the fluids of the vehicles to be heated (or the ambient temperature) rises above the set points, the heating devices can be shut off, until such point as the temperature of the vehicle fluids sink below the set point level.

One feature of the present invention is that it enables the user to supply heat to a vehicle on an intermittent rather than a continuous basis; or else, on a basis wherein heat is supplied to a vehicle only during a portion of its idle period, rather than its entire idle period.

In tests conducted on the instant invention, the Applicant found that some conventional block heaters of the type used with typically commercial vehicles are capable of heating the fluids within the vehicle up to an acceptable point (typically, the set point of 25° F. or greater) after about six hours of continuous heating.[1]

[1] This hypothetical assumes a 0° F. low temperature during the idle period of the vehicle. It will be appreciated that if the average temperature during the idle period is greater than 0° F., the recovery time accessary to heat the vehicle to a point above the set point may be significantly less than six hours. Additionally, it will also be appreciated that different types of vehicles may require longer heating times, and that extreme temperatures, such as the ones one might encounter in the Winter in Northern Canada and Alaska may require longer recovery times. However, for purposes of illustration within this application, the assumption is made that a six-hour heating period is a preferred heating period for heating a vehicle during an idle period. This hypothetical is carried through the application and is provided for explanation and not limitation.

Return now to the hypothetical example of the school buses that will park at 6:00 p.m., and then restart the next morning at 6:00 a.m. As only a six-hour period is usually required to fully heat the fluids within the school bus to a point wherein they are at the set point, there is no need to run the heating device for the entire 12-hour idle period. Rather, the controller of the present invention can control the flow of electricity between the electrical outlet and the device heater, so that heat is only applied to the bus during the necessary six-hour recovery period prior to the restart of the vehicle. As such, the block heaters can be turned off between 6:00 p.m. and midnight, and then restarted at midnight for a six-hour recovery period, so that by 6:00 a.m. when the buses are restarted, the fluids within the buses are then at or near the set point.

This use of the device of the present invention has the potential to save considerable amounts of electricity over the weekend. For example, on the weekend, the bus will likely be shut off and parked at about 6:00 p.m. Friday night, and remain idle all-day Saturday and all-day Sunday, with the bus not being restarted until Monday morning at 6:00 a.m.

With a conventional heating device, the bus would be plugged in on a Friday night, and continuously heated for a 60-hour period until the buses were unplugged and restarted on Monday morning. With the present invention, the timer of the controller of the present invention can be programmed to keep the block heaters in a "off" position until Sunday night at midnight. The heaters would then be turned on for a six-hour period (or whatever recovery time period was appropriate), that would be sufficient to heat the buses up for starting on Monday morning at 6:00 a.m. Through this operation, only six hours of electricity would be drawn to operate the device, rather than the current device requiring a 60-hour operation.

It is also a feature of the present invention that the device can be programmed not to actuate the device heater to operate until the ambient temperature falls below a certain "set point". As discussed above, most vehicle engines do not require the use of a block or coolant heater until the temperature falls below about 25° F. Therefore, one can save electricity by programming the present invention to not actuate the block and coolant and/or fuel heaters to operate unless the ambient temperature falls below the set point.

This saves electricity, because the standard operating procedure at many fleet facilities is to plug in and turn on the block heaters, even on nights when the temperature does not sink below 25° F. This is done because temperatures are largely unpredictable, and the fact that the costs incurred by not having a vehicle operational are greater than the cost of running a block heater all night during the Winter.

It is another feature of a most preferred embodiment of the present invention, that the controller can be programmed to operate so that it is capable of actuating the device to either operate for a shorter period of time than the normal hypothetical five-hour recharge time, if conditions warrant. One circumstance where conditions so warrant is where the ambient temperature does not fall below the set point until sometime after the device would normally begin operation. For example, if the set point is set at 25° F., and the ambient temperature when the bus is turned off at 6:00 p.m. is 30° F., there would be no need to turn the block heater on. If the ambient temperature did not drop to 24° F. until 3:00 a.m., there would be no need to actuate the block heating device until the temperature actually went below the 25° F. set point. In the above hypothetical, the heaters would be actuated to operate during the remaining recharge period between the time when the temperature actually fell below the set point and the bus was restarted; or alternately, between the time when the temperature falls below the set point and then the temperature once again rises above the set point, whereupon the device would be programmed again to turn off These and other features will become apparent to those skilled in the art upon a review of the drawings detailed description and claims of the present invention that are presented below.

BRIEF DESCRIPTION OF DRAWINGS

FIG. 5 is a first screen shot view of the present invention showing the screen display normally encountered upon turning the device on;

DETAILED DESCRIPTION OF THE PREFERRED EMBODIMENT

Figure 1:
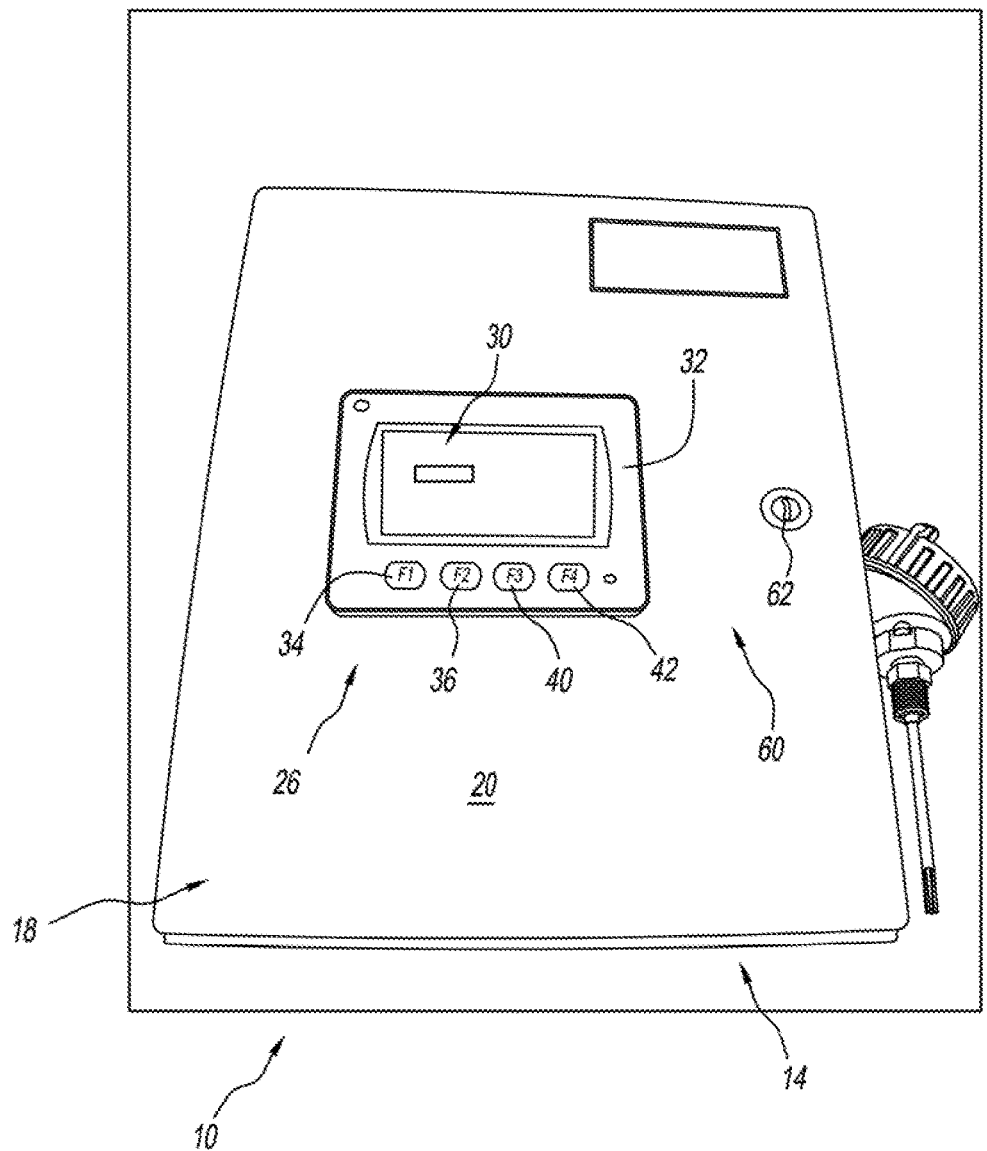
FIG. 1 is a front view of the exterior of the case of the controller of the present invention showing the input screen thereon.

The description that follows describes, illustrates and exemplifies one or more particular embodiments of the present invention in accordance with its principles. This description is not provided to limit the invention to the embodiment or embodiments described herein, but rather to explain and teach the principles of the invention in such a way to enable one of ordinary skill in the art to understand these principles and, with that understanding, be able to apply them to practice not only the embodiment or embodiments described herein, but also other embodiments that may come to mind in accordance with these principles.

The scope of the present invention is intended to cover all such embodiments that may fall within the scope of the appended claims, either literally or under the doctrine of equivalents.

It should be noted that in the description and drawings, like or substantially similar elements may be labeled with the same reference numerals. However, sometimes these elements may be labeled with differing reference numbers, such as, for example, in cases where such labeling facilitates a clearer description. Additionally, the drawings set forth herein are not necessarily drawn to scale, and in some instances proportions may have been exaggerated to more clearly depict certain features. Such labeling and drawing practices do not necessarily implicate an underlying substantive purpose.

Furthermore, certain views are side or sectional views which depict only one side of the device (or one set of components of a multi set array of components). However, it will be understood that the opposite side and other component sets are preferably identical thereto. The present specification is intended to be taken as a whole and interpreted in accordance with the principles of the present invention as taught herein and understood by one of ordinary skill in the art.

A. Overview

In its most preferred embodiment, the present invention relates to a centralized fleet management control device that comprises an intelligent operator control panel (IECP) that through software logic, limits the flow of electricity to a vehicle fluid heater, such as an engine block heater. In doing so, fleet maintenance electrical usage can be reduced substantially, and reduced by more than one half from some prior known devices.

The device includes a central, programmable, logic controller (PLC) that manages a plurality of independent and separately controllable vehicles or pluralities of vehicles. For example, one embodiment can manage four separate and independent "zones" of heart receptacles that have the potential to control the operation of 40 electrical outlet receptacles, that, usually converts into about 40 different vehicles.

The engine block heaters of the present invention warm fluids prior to vehicle start up. Although pre-warming fluids such as oil, coolant and gas is not necessary in warmer weather, such heating devices are used in colder weather to overcome the difficulties starting engines caused by the increased fluid viscosity that results from lower temperatures. Applicants believe that no commercially available device exists that is capable of centrally controlling vehicle pre-heat devices on fleet type vehicles, such as commercial, military, transit and school bus vehicles. Timers and devices exist in outside receptacles, known devices have certain drawbacks.

The present invention employs the intelligent electrical control panel (IECP) to manage the flow of electricity between an existing power source, such as an electrical panel, and the electrical source that provides electricity to the electrical panel and the outside receptacle that is placed in the parking lot in which the vehicles reside when they are idle.

The IECP includes a programmable logic controller (PLC) that is capable of controlling the flow of electricity preferably to a plurality of outside receptacles that provide power for vehicle heating devices. A temperature sensing input source, such as a thermocouple that is provided for sensing outside temperature at a predetermined location that is correlative to the temperature in which the vehicles reside. Preferably, the thermocouple senses outside temperature at a location that is correlative with the temperature of the vehicle. One example of such a correlative location is the parking lot close to the receptacle and idled vehicles.

The temperature sensor should preferably sense the temperature that is similar to or close to the temperature experienced by the vehicle and thus, should be placed close to the vehicle. If the vehicles are stored outside, the temperature sensor should also be positioned outside to record outside temperatures. In contrast, if the vehicles are stored indoors in a garage, the temperature sensor should be positioned indoors, so that it senses the temperature in the garage in which the idled vehicles are placed.

The temperature sensing thermocouple is in communication with the controller communicating temperature related information to the PLC. The intelligent electrical control panel (IECP) synchronizes outside temperature, temperature set points that govern activation control calendar, week days, start time and end time to optimize electrical usage for multiple receptacle heating devices.

Preferably, the intelligent electrical control panel (IECP) is permanently installed next to an existing electrical fuse or circuit breaker panel. The intelligent electrical control panel has the potential to be connected to a central energy management system where available, such as an Alerton (Bactalk) building automation system. Through this communication, the IECP can provide information to the central energy management system that allows the end user to have real time, energy savings information, and remote control over the intelligent electrical control panel.

The intelligent electrical control panel continuously receives input from the thermocouple to use the temperature as a key input driver for the logic of the programmable logic controller. In a most preferred embodiment, the programmable logic controller employs a temperature set point to turn on the circuit and a second temperature set point to turn off the flow of electricity. The first temperature set point enables the electrical circuit to permit (but not necessarily start) flow of electricity if the temperature sensed by the temperature sensor falls to a temperature at or below the Below-Turn-On set point.

A second temperature set point is typically set at a temperature higher than the Below-Turn-On set point, and comprises the Above-Turn-Offset point. The Above-Turn-Off set point is a set point where at the controller is programmed to not allow the flow of electricity to flow between the control panel and the fluid heaters, as the temperature above the Above-Turn-Off set point is high enough so that further warming of the vehicle fluids is unnecessary. In a most preferred embodiment, the separation between the Below-Turn-On set point and the Above-Turn-Off set point may be something on the order of five to twenty degrees Fahrenheit and more preferably between about five and fifteen degrees Fahrenheit.

In one most preferred embodiment, the Applicants found that a very workable temperature for the Below-Turn-On set point was 32 degrees Fahrenheit. This 32-degree Fahrenheit Below-Turn-On set point works well because at 32 degrees or above, the increased viscosity of the oil and other fluids is not so great, and the battery is not so weakened, so as to prevent a normal battery from starting the vehicle quite reliably, notwithstanding the increased difficulty of doing so, when compared to the difficulty of starting a vehicle at a higher temperature such as 70 degrees Fahrenheit. However, the Applicants have also found that at temperatures below 32 degrees, the ability of the vehicle to start becomes impeded because the great viscosity of the oil and the weakened power of the battery.

From employing the temperature set points and algorithms that correlate factors such as vehicle temperature, time remaining until the end of the idle period, and time required to heat fluids the number of degrees necessary to cause the fluids to be at a desirable, achievable temperature, the program logic controller can be operated in a manner that actuates the vehicle heater to operate only during a portion of the time that the vehicle is idle and not running, rather than the entire time during which the heating device is plugged into the electrical receptacle. As such, the user can plug the heating device into the electrical receptacle to electrically couple the controller to the vehicle heater without causing the heater to begin drawing electricity immediately. Rather, the heater only begins to draw electricity to heat fluid at the time so designated by the programmable logic controller. As such, the electricity is only drawn intermittently during the idle period rather than constantly during the idle period, which thereby reduces the amount of time that the heating devices are actuated which thereby reduces the electrical consumption of the heater device.

In the most preferred embodiment, the device includes a zone circuit control, in which the vehicle receptacles attached to the zone are divided up into a plurality (such as four) independently operable and separately controllable zones. Each of the four zones can be programmed independently with those parameters that are best designed to deal effectively with the particular vehicles attached to the zone. For example, some zones will employ different time on and time off regimes to compensate for vehicles that are used at different time periods and are idled at different time periods. Others, may be differentiated based on Below-Turn-On set points and above offset points, as different types of vehicles (e.g. diesel engine vehicles) may be more adversely affected by cold temperatures than other types of vehicles (e.g. gas engine vehicles).

The following hypothetical zone example will help to illustrate the value of the independent and separate programmability of various zones. Hypothetically, imagine a 20-vehicle fleet, where four of the 20 vehicles are set aside for emergency use.

In such a case, the controller can be figured to only activate the engine heater during an interval just prior to the end of the idle period for a duration of time that is the minimal generally necessary to heat the engine fluids up to the desired temperature, so that the engine fluid being heated reaches the desired fluid temperature at some time near the end of the idle period. In contrast, the controller can direct electricity to the emergency vehicles, so that energy is fed intermittently over the duration of the idle period, such that heat is applied to the fluids whenever the fluid temperature or ambient temperature falls below a relatively higher Below-Turn-On set point, and that the electricity flow is cut off to the heaters after a time interval, that is calculated to keep the fluid temperatures close to or at the desired fluid temperature to maximize the ease of starting.

For example, if 32 degrees Fahrenheit is the desired temperature, the controller might determine that the most efficient way to maintain the fluid temperature at a desired 32-degree fluid temperature is to intermittently apply electricity to the fluid heater for 10 or 15 minutes during every half hour interval.

An additional feature of the zone circuit design of the present invention is to use the programmable logic controller to provide a soft start of the various circuits within the zone. As discussed above, there may be a plurality of zones (such as four), with each zone carrying 10 or more receptacles. As engine block heaters can draw up to 1500 watts of power and 1400 amps of electrical current per receptacle, it will be appreciated that starting all of the circuits at the same time could cause unnecessary power surges and spikes.

The programmable logic controller can be programmed to insert a timed delay between activations of each zone, or among receptacles within a zone, so as to stagger the "turn on" times of the receptacle, to thereby minimize the likelihood of such spikes occurring.

Another most preferred embodiment of the present invention employs a calendar week day control feature that is programmed by the interaction of the input device and timer. This control feature enables control of the vehicle heater to be based upon the particular calendar day of the week. For example, the device can be designed to operate on a different idle time schedule on a calendar weekday when the vehicles, such as school buses are in operation while operating on another idle time regime during another idle regime during weekends and holidays, when the vehicles are not operating.

The device can be programmed to never allow electricity to be transmitted to the vehicle heater on a Saturday or Sunday, unless the program is either manually over-ridden, or certain parameters are encountered. Such parameters may include extremely cold temperatures that would make it advisable to activate the vehicle heaters on days when the vehicles are not likely to be used.

The logic controller has a time on, time off feature that is used to program the idle period start and idle period end time. By using the programmable logic controller's timer and clock feature, the circuits can be accurately turned on at a predetermined time to optimize the effectiveness of the heating devices.

In many cases, the heating devices may only require five hours of on time to raise the temperature of the fluid to the desired temperature, under ambient temperature conditions that may for example, be at zero degrees. Without the clock feature, the device would likely supply heat to the vehicle all night, thus using 12 hours of electricity, rather than the five hours used by the present invention For example, vehicles that will park at 6:00 p.m. and then restart the next morning at 6:00 a.m. may only require a five-hour period to preheat the engine fluids. As such, there is no need to run the heating device for the entire 12 hour idle. Rather, the IECP of the present invention controls the flow of electricity to the electrical receptacle heating device, so that heat is only applied to the vehicle during a necessary five-hour recovery period that is immediately prior to the end of the idle period, which is the time at which the vehicle is likely to be started. As such, the vehicle block heaters in the above hypothetical can be turned off between 6.00 p.m. and 1.00 a.m. and then restarted at 1:00 a.m. for a five-hour recovery period that would terminate at 6:00 a.m., which is the end of the idle period from the time at which the vehicles are restarted. At this point, after five hours of applied heat, the temperatures of the fluid would have reached the desired, predetermined fluid temperature.

As a further example, weekend scheduling can also be deployed. For example, the hypothetical control system that employs four zones, with each zone controlling ten electrical circuits, it is desirable that if the temperature so warrants the five-hour recovery period, that the circuits turn on to allow electricity to flow to the heaters on Monday through Friday mornings at 1:00 a.m., and to turn off at 6:00 a.m. However, when the vehicles return to the parking lot, after the end of the morning run, (in the case of school buses), a second attribute screen can be employed on the input to turn the circuits on, supply electricity as necessary between 9:00 a.m. when the vehicles arrive, and 2:00 p.m. when the vehicles restart for their afternoon runs.

Depending upon temperature, the mid-afternoon regime of the control circuits can be similar to the evening regime. For example, if it requires only three hours of heat to be supplied to the vehicle to enable the fluids to rise to the desired level, the device can be controlled so as to not allow current to flow to the heaters from 9:00 a.m. to 11:00 a.m., but to allow heat to flow through the heaters between 11:00 a.m. and 2:00 p.m.

As another example, it is typical for a portion of a school bus fleet to be used differently than the remainder of the school bus fleet, as this portion may be used for weekend and evening activities. In such a case, the vehicles in this "enhanced activity" group (such as zone 2) can be programmed so that the circuits operate even on Fridays and Saturdays and holidays, when otherwise there would be no electricity and heat supplied to the larger portion of the fleet.

An additional feature of the present invention is that the programmable logic controller can be programmed so as to operate for a shorter period of time than the "normal" five hour "recovery time" if conditions warrant. For example, in circumstances where the ambient temperature adjacent to the vehicles is not as cold as the "standard time", a shorter recovery time may be necessary. Another example is where the ambient temperature during the interval period climbs above the Below-Turn-On temperature. A third example is where the ambient temperature does not fall below the Below-Turn-On temperature until sometime during the five-hour window when the device would normally be supplying electricity to the heater.

Presented below are Tables 1 and 2 that employ temperature data from three cities (here, Boston, Indianapolis, and Minneapolis) during the months of November, December, January, February and March, indicate the number of days (Table 1) and hours (Table 2) when heat would need to be applied to a vehicle to place the fluid temperatures at an appropriate temperature

| | Days Active | | | |
|---|---|---|---|---|
| | Boston | Indianapolis | Minneapolis | Base Case |
| Nov. | 8 | 11 | 15 | 30 |
| Dec. | 11 | 15 | 21 | 31 |
| Jan. | 20 | 21 | 22 | 31 |
| Feb. | 17 | 18 | 20 | 28 |
| Mar. | 12 | 10 | 17 | 31 |
| Total | 67 | 75 | 94 | 151 |
| % Days On | 55% | 50% | 38% | 100% |

| | Hours Active | | | |
|---|---|---|---|---|
| | Boston | Indianapolis | Minneapolis | Base Case |
| Nov. | 38 | 53 | 75 | 456 |
| Dec. | 53 | 73 | 103 | 468 |
| Jan. | 98 | 107 | 110 | 468 |
| Feb. | 85 | 92 | 100 | 432 |
| Mar. | 62 | 50 | 83 | 468 |
| Total | 337 | 375 | 472 | 2292 |
| % Savings | 85% | 84% | 79% | 100% |

For example, in January, there are 20 days in Boston and 22 days in Minneapolis wherein it would be necessary to apply heat to a vehicle heater. Because the prior an devices do not have the control features of the present invention, it is likely that fleet operators would connect the heaters every night during every one of the 31 nights in January. However, because of the temperature sensing and controllable nature of the present invention, electricity would only be supplied to vehicles in Boston for 20 days and Indianapolis for 21 days, and in Minneapolis for 22 of the 31 days. As such, heat would not be applied during 9, 10 or 11 days of each month, thus saving electricity, as no electricity would be used during these 9, 10, or 11 days respectively.

Turning now to Table 2, it will also be noted that there is a great potential for savings to be achieved because of the reduced number of hours. For example, in January in Boston, the device would be used 20 days. However, during those 20 days, the present invention might only use the device for 98 hours or approximately five hours per day. In contrast, the 20 days in Boston that would be used with an uncontrolled device of the prior art would likely require the use of 486 hours of electricity that would need to be delivered of the fluid heating device. This results in a significant savings of electricity, and hence, money for the users.

The following is based on the assumption of temperatures recorded during 2016 in the cities listed above, with the "below" set point being set at 32 degrees Fahrenheit, the "weekend off" feature being active and the five hours "on time" being employed just prior to the end of the idle interval.

For the base time, it is assumed that electricity will be fed for 12 hours each day between Monday and Friday, and 24 hours on Saturday and Sunday. It is also assumed that a five-month winter season is used, that extends between November and March.

B. The Device and Method Shown in the Drawings

Figure 1A:
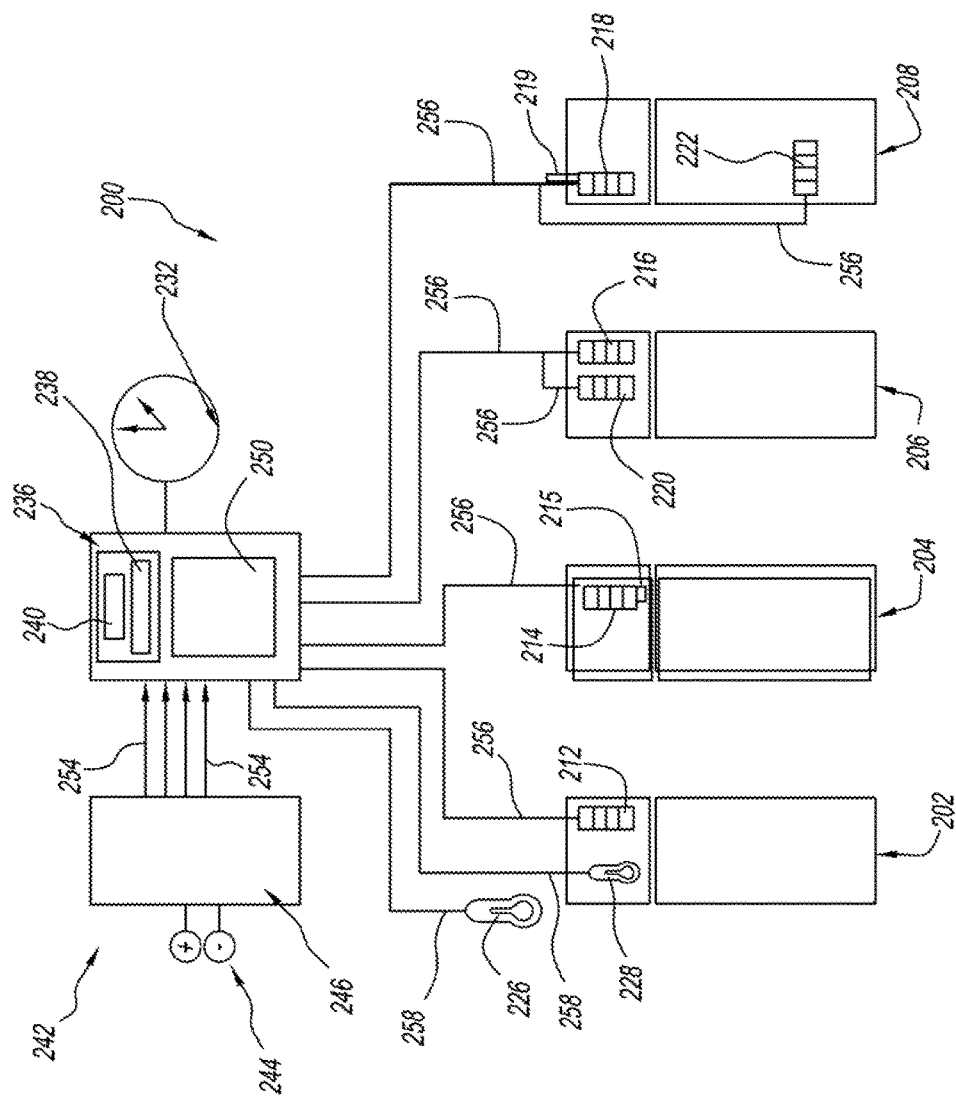
FIG. 1A is a schematic view of the components of the present invention.
Figure 1B:
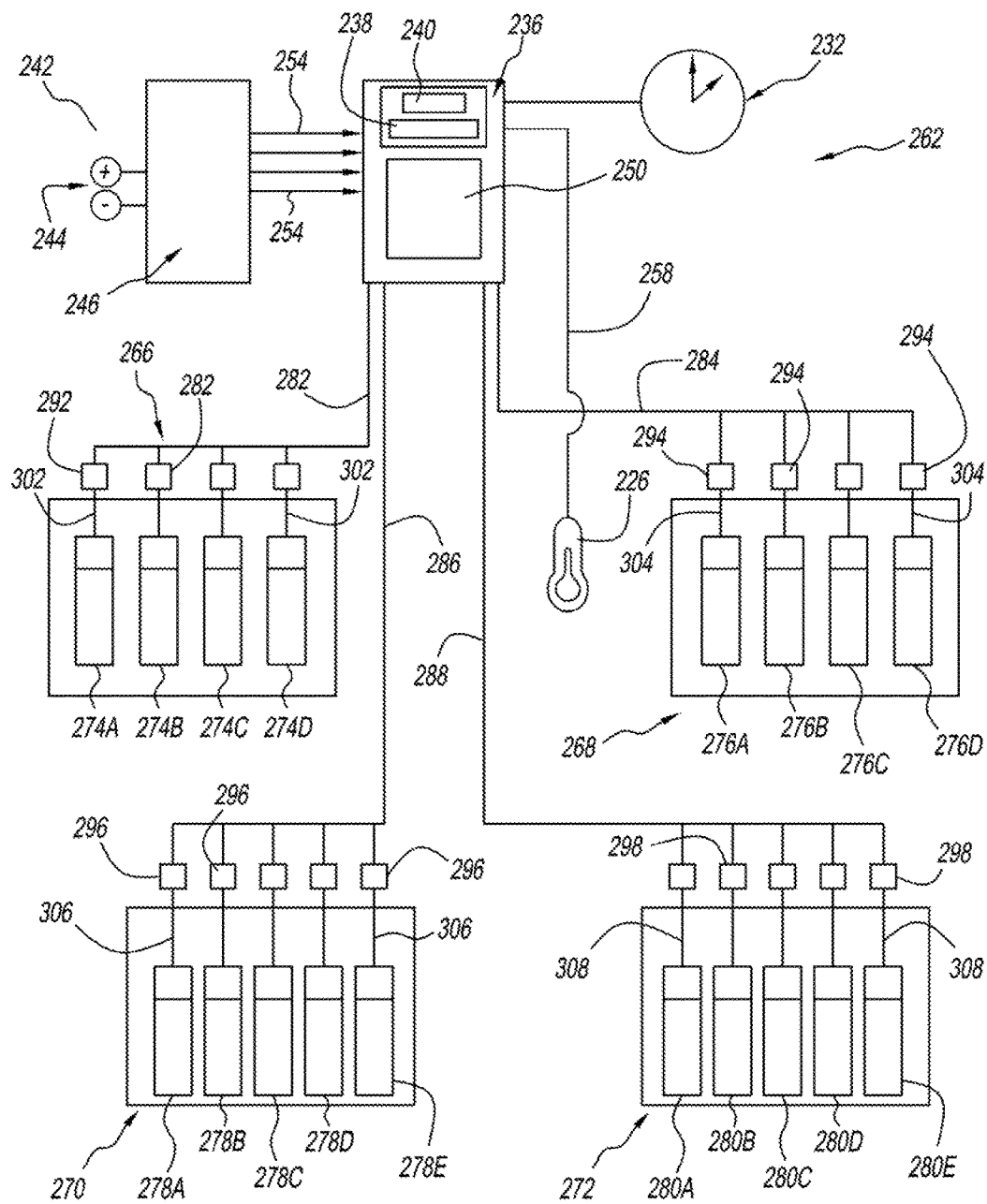
FIG. 1B is a schematic view of the components of the present invention and the multi-zone environment in which it operates.
Figure 1C:
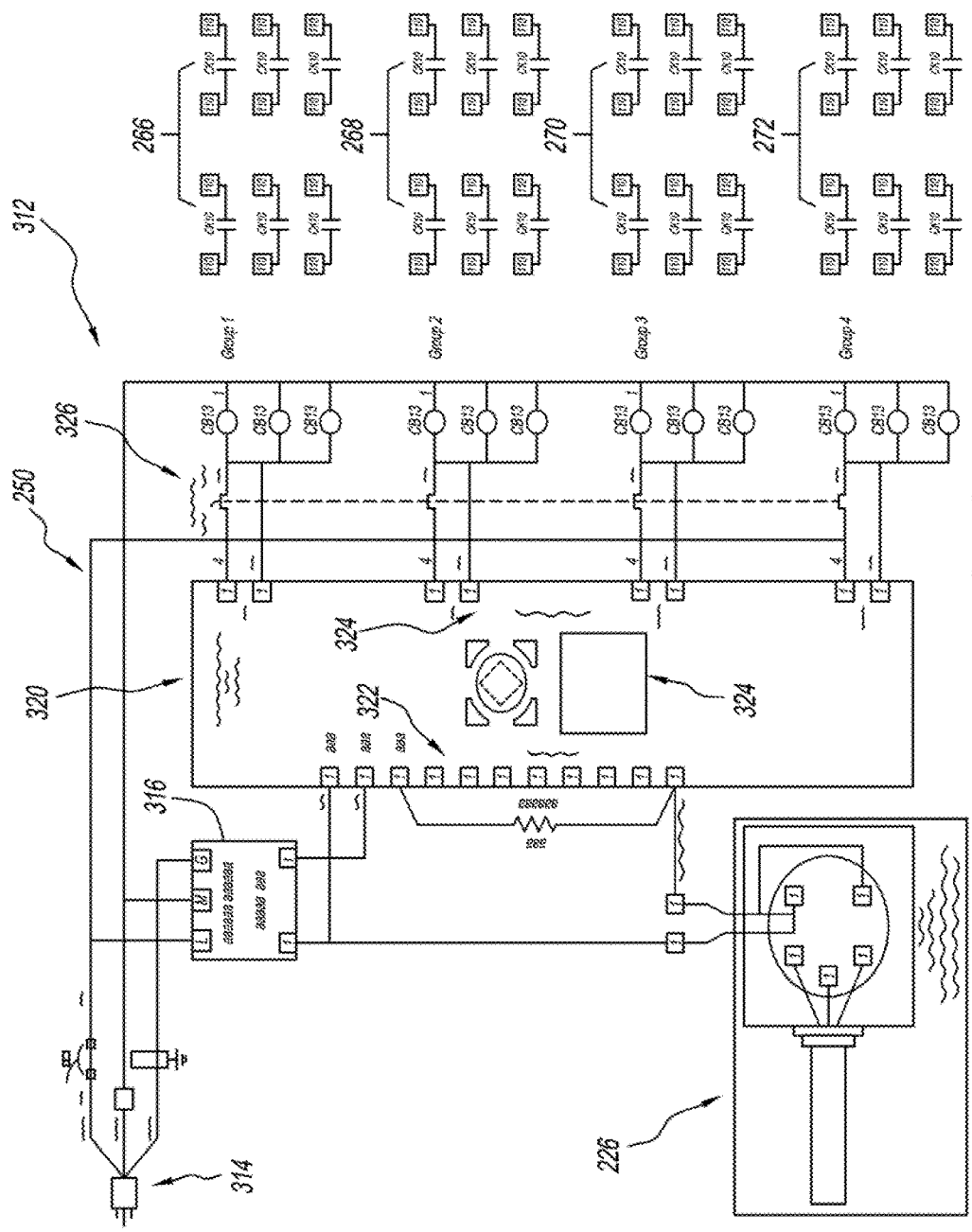
FIG. 1C is a circuit diagram of the present invention for illustrating the electrical components and relationships of the present invention.

Your attention is now directed to FIG. 1B and 1C.

FIGS. 1B and 1C show a vehicle fluid heating system 200 that is provided for achieving an elevated pre-determined fluid temperature for a plurality of vehicles, such as a first vehicle 202, a second vehicle 204, a third vehicle 206 and a fourth vehicle 208.

Although the vehicles 204-208 are seen as single vehicles, the vehicles can represent groups of vehicles, so that the term first vehicles can also serve to mean first group of vehicles or first zone of vehicles. In the drawings, the vehicles are shown as school busses, as the present invention is particularly well adapted for use with school bus fleets. However, the device is also well adapted for use with all fleets of vehicles. including commercial, consumer and institutional vehicles. Since the device is primarily designed for use with fleets, it is envisioned that it will be used primarily with commercial and institutional vehicles, such as tracks and busses, rather than individual consumer automobiles.

The vehicle fluid heating system is provided for keeping the fleet of at least two vehicles 202-208 at an elevated temperature during an idle period having a duration defined by a start point and an end point. As discussed above, the start point usually comprises the point at which the vehicle is finished for the day, such as after the school bus has made its last run, and the end point usually comprises is the time, such as 6:00 a.m. when the bus is started to begin its morning route.

A vehicle fluid heater is provided for each of the devices, including a first vehicle fluid heater 212, a second vehicle fluid heater 214, a third vehicle fluid heater 216 and a fourth vehicle fluid heater 218. The second vehicle fluid heater 214 includes an actuator 215, as fourth vehicle fluid heater 218 also includes an actuator 219. The actuators 218 and 219 are "on off switches" that enable the user to turn on and off the heater at the site of the heater.

In most cases, the vehicle heaters that can comprise heater probes are turned on and off by plugging them into or removing them from receptacles, such as receptacle 292, 294, 296 and 298 shown in FIG. 1B. However, actuators 218-219 present an additional on off switch. Actuator 215 is shown as a fluid sensor actuator. For example, this sensor can be designed to only allow the heater 214 to run if the actuator 215 senses the presence of fluid. If the fluid in the tank falls below a certain level, so that the heater probe 214 is disposed in air rather than fluid, it may be desirable not to allow the heater to impart heat to the vehicle.

Actuator 219 is a manual push button type actuator or on off switch actuator that the user could actuate to turn on or off manually. A manually operable actuator 219 might have great use in connection with rental fleet vehicles, such as rental buses or excavators or power shovels that are not used on a regular basis. For example, a power shovel or excavator owned by a rental company, may spend days or weeks in the storage lot between uses. In such a case, the most convenient way to handle the device may be to allow the heaters to be hooked up to a source of electricity but turned off (with actuator 219) so that they were not drawing electricity or heating the fluids. On the day prior to the day on which a rental is scheduled, the operator could actuate the button 219 to turn on the heater and place it in its normal cycle, so that when the device was rented in the morning, the fluids would be heated up to a point where the device would start easily.

It should also be noted that auxiliary vehicle heaters 219, 222 are employed. Auxiliary heater 220 is shown being placed in the hood compartment, along with primary heater 216. This use of two heaters might occur if one heater was used to heat one vehicle fluid such as transmission fluid, and the auxiliary heater 220 was used to heat a second fluid, such as vehicle coolant or vehicle oil.

Auxiliary heater 222 is shown being placed in the rear of the vehicle, and is used to schematically indicate that the heater 222 may comprise a fuel heater that is disposed within the tank of the vehicle, so as to prevent the fluid within the tank from freezing up, and making the fluid sufficiently less viscus to enable the fluid to flow through the fuel line.

A temperature sensor 226, such as a thermocouple is provided for sensing a temperature of a temperature source that has a correlative relationship to the fluid of the vehicles. For example, if the vehicles 202-208 are parking outside, the correlative source may be some place outside, so that the thermometer 226 measured the same ambient temperature that was being experienced by the busses. However, if the buses were kept inside in a marginally heated garage, the thermometer 226 would probably best be placed within the garage, rather than outside, as the ambient temperature being experienced by the buses within the garage would likely be warmer than the outside temperature.

A thermocouple 228 could be placed within a fluid reservoir of one of the vehicles, as is shown in FIG. A. By putting a thermocouple 228 on the vehicle, one could measure the fluid temperature within the fluid reservoir. This fluid temperature would give the user a reading of the temperature of the fluid, that may provide a more accurate means for determining the time necessary to apply heat to the fluid, and thereby use electricity than a thermometer that just measured the ambient temperature in the area in which the buses or vehicles were placed during their idle period.

A settable timer 232 is provided for enabling the user to establish the start point and the end point of the idle period of the various vehicle heaters 212, 222. The settable timer is shown in the drawings as being a separate timer. However, in practice, the settable timer will likely be a timing program or circuit that is contained within a controller 236.

The controller 236 is in communication with an electrical source 242 for controlling the flow of electricity from the electrical source 242 to the various vehicle fluid heaters 212, 222. The controller 236 is also in communication with the temperature sensor 226, 228 for receiving temperature information, and is in communication with the settable timer 232 for obtaining information about the start point and end point of the vehicle idle period.

The controller is shown as including a screen 240 for providing information to the user, and an input device such as a keypad 238, that the user can employ to input information into the controller 236. The controller 236 includes a processor for receiving the temperature information from the settable timer 232, idle start points information, period end point information, to enable the controller to determine a vehicle fluid heating interval having a duration that is less than the duration of the idle period, while still achieving the elevated, pre-determined fluid temperature at the end of the idle period. A switch actuator, such as a set of relay switches 250 are provided for allowing the flow of electricity from the electrical service 242 to the fluid heater 212, 222 during the fluid heating interval.

The electrical source generally comprises a power line 244 that is led into a junction box or control panel 246 that includes a plurality of circuit breakers. Electrical conduits 254 are in electrical communication with the controller 236, and the switching relays 250.

A further set of electrical conduits 256 convey the current to the vehicles. As is best shown in FIG. 1B, the electrical conduits 282, 284, 286, 288 convey the current to a plurality of receptacle outlets 292, 294, 296, 298. Power cords 302, 304, 306, 308 then convey the current from the receptacles 292, 294, 296, 298 to the buses 274A-D, 276A-D, 278A-E and buses 280A-E.

It should be noted that the input device 238 enables the user to input operational data into the controller. This operational data includes such things as idle periods, start point and end point data. Additional information can also be input, as is discussed in more detail below.

The timer member 232 can include a calendar function for enabling the user to use the input device 240 to input operational data for a variety of days, wherein the operational data for the various days is different. For example, the user can input one set of idle start point and end point data for weekdays and a different set for weekends if the buses or other vehicles are used differently on the weekdays than they are on the weekends.

It should also be noted that the processor and controller are capable of setting different parameters for the various vehicles that are in a manner that is separate and independent from each other. As such, the parameters set for vehicle 202 may be entirely different than those set for vehicles 204, 206, or 208. As discussed below, all of the vehicles within a particular fleet may not be used in a similar manner. Therefore, it is important to have the ability to program a particular vehicle heater or a particular sets of vehicle heaters to operate under different parameters than the heater for other vehicles.

Several methodologies exist for determining the heating interval to be employed with a particular vehicle. For example, one methodology is to determine the ambient temperature, and then use the ambient temperature to determine a time that is necessary to heat fluid from that ambient fluid to the desired temperature. If this time period were five hours and if the end of the idle interval were to occur at 6:00 a.m., the controller would then be programmed to allow electricity to flow to the vehicles, and thereby begin heating the vehicle at 1.00 a.m., thus providing a five-hour heating period.

Another methodology would be to measure the ambient temperature, and calculate the time necessary to heat the fluid from that ambient temperature to the desired temperature, and then begin the heating process when that time period comprises the time period between the time at which the electricity is turned on and the end of the idle interval. This would vary the heating interval on a daily basis. For example, if the ambient temperature at 1:00 a.m. were 28 degrees, and the time required to heat fluid from that ambient temperature (28 degrees) to the desired end point temperature (e.g. 32 degrees) was 40 minutes, the controller would not turn the heaters on until 40 minutes before the end of the idle period, or at 5:20 a.m., assuming that the temperature got no colder than 28 degrees.

However, if the temperature continued to decrease so that at 3:30 a.m. a low temperature point was reached of 23 degrees which required a two-hour fifteen-minute heating interval, the controller would turn the heaters on then at 3:45 a.m., to provide the appropriate heating interval before the idle period end time.

The system could also include an override function, that would allow the user to override the timing interval imposed by the system. This override switch would comprise a manual actuator such as 219, that might be directly coupled to the heater 218. Alternately, the override function could be a function that one would program into the controller using the input pad 238. Such an override function might be used, if for example, a sudden need arose to warm a bus up where such was not expected before hand.

Turning now to FIG. 1B, another exemplary arrangement is shown. The primary difference between the arrangement of FIG. 1A and FIG. 1B is that FIG. 1A consists of a plurality of zones 266, 268, 270, 272. Each of the zones includes a plurality of buses. Zones 1 and 2, 266, 268 are shown as including four buses 274A-D, 276A-D. Zones 3, 270 and 4, 272 are each shown as having five buses 278A-E, 280A-E. In actuality, it is envisioned that most zones will be designed to contain up to 10 buses.

Each of the zones are actuated by the controller on a "zone" basis, such that all the buses 274A-D of zone 1 are treated alike. It will be noted that FIG. 1B does show the use of receptacles 292, 294, 296, 298 to which the electricity is directed, and to which power code 302, 304, 306 are plugged in order to provide electricity to the various buses.

As will be described in more detail below, it is contemplated that although the buses within a particular zone will be treated identically, that buses in different zones, such as zone 266 and 268 may be treated differently. For example, the buses in zone 268, 270 and 272 may all comprise regularly scheduled buses, that operate from 6:00 a.m. to 10:00 a.m. on morning runs and then from 2:00 p.m. to 6:00 p.m. on their evening runs, with no operation during evenings and weekends. As such, these buses would have idle intervals that would start at 10:00 a.m. and 6:00 p.m. on weekdays, and would end at 2:00 p.m. and 6:00 a.m. on the weekdays. During the weekends, the idle interval would exist from approximately 6:00 p.m. Friday to 6:00 a.m. Monday.

In contrast, the buses in zone 266 may comprise activity buses. Activity buses are buses that may be used for after school activity, and for weekend activities.

Since most activities would be confined to after school periods until about 10:00 or 11:00 p.m., and on weekends on Saturdays, the buses of zone 266 might be programmed to have interval periods that started at 10:00 a.m. ended at 2:00 p.m., and then started again at 10:00 p.m. and ended at 6:00 a.m., on the week days, and included idle intervals that ended at 6:00 a.m. on a Saturday and began at 7:00 p.m. on a Saturday with the 7:00 p.m. Saturday idle interval ending at 6:00 a.m. Monday.

FIG. 1C shows a wiring diagram for the controller switching arrangement of the present invention, and includes a controller relay unit 312 that derives its power from power source 314 for controlling the operation of the controller. The AC current from the controller is fed into a power supply 316 that converts the power from AC to DC. A programmable relay base unit is provided that includes DC inputs 322 for receiving power from the power supply, relays 327, and relay outputs 324 that direct current out of the relays.

The current that emerges from the relays is then sent to a zone control 326 for controlling the various zones 266, 268, 270, 272 that are generally functionally similar to the zones of the same numbers shown in FIG. 1B.

A controller 10 of the present invention is shown in FIG. 1. The controller 10 includes a housing assembly 14, that is preferably an electrical service grade steel housing 14 having a door 18 thereon, that is hingedly coupled to base 16 of the housing the door 18 is moveable between an open position and a closed position. A lock member 60 is provided for enabling the door 18 to be locked onto the base 16, to thereby prevent unauthorized access to the interior of the housing 14. Preferably, the housing 14 has a depth of four to five inches so that components can be placed within the interior of the housing 14.

A particularly suitable panel housing used in the preferred embodiment is what is referred to as a "NEMA-12 box". A NEMA-12 box is generally a general-purpose type of electrical box that is intended primarily for indoor use. The device is designed to provide some protection against dust, falling dirt and dripping non-corrosive liquids. A NEMA-12 is one that meets appropriate drip, dust and rust resistant tests for electrical service use.

A wide variety of NEMA-12 enclosures are provided from a variety of manufacturers, including Hammond Manufacturing and ATK Electric Supply of 6555 Corporate Drive, Cincinnati, Ohio 45242.

Although the NEMA-12 box works well for indoor uses, a NEMA-4x box is better adapted for outdoor use. A preferred NEMA-4x box may have generally the same size and shape configuration as the NEMA-12 box shown in FIG. 1, a NEMA-12 box differs from a NEMA-4x box in that a NEMA-4x housing is designed to better resist snow, rain, wind and other outdoor conditions that require more ruggedization than a box, such as a NEMA-12 box that is designed primarily for indoor uses.

The NEMA-12 box shown in FIG. 1 has dimensions of approximately 18 inches tall by 12 inches wide and about 8 inches in depth. The size of the housing 14 can be either larger or smaller, depending upon the number and size of the components that will be placed within the housing 14.

Figure 2:
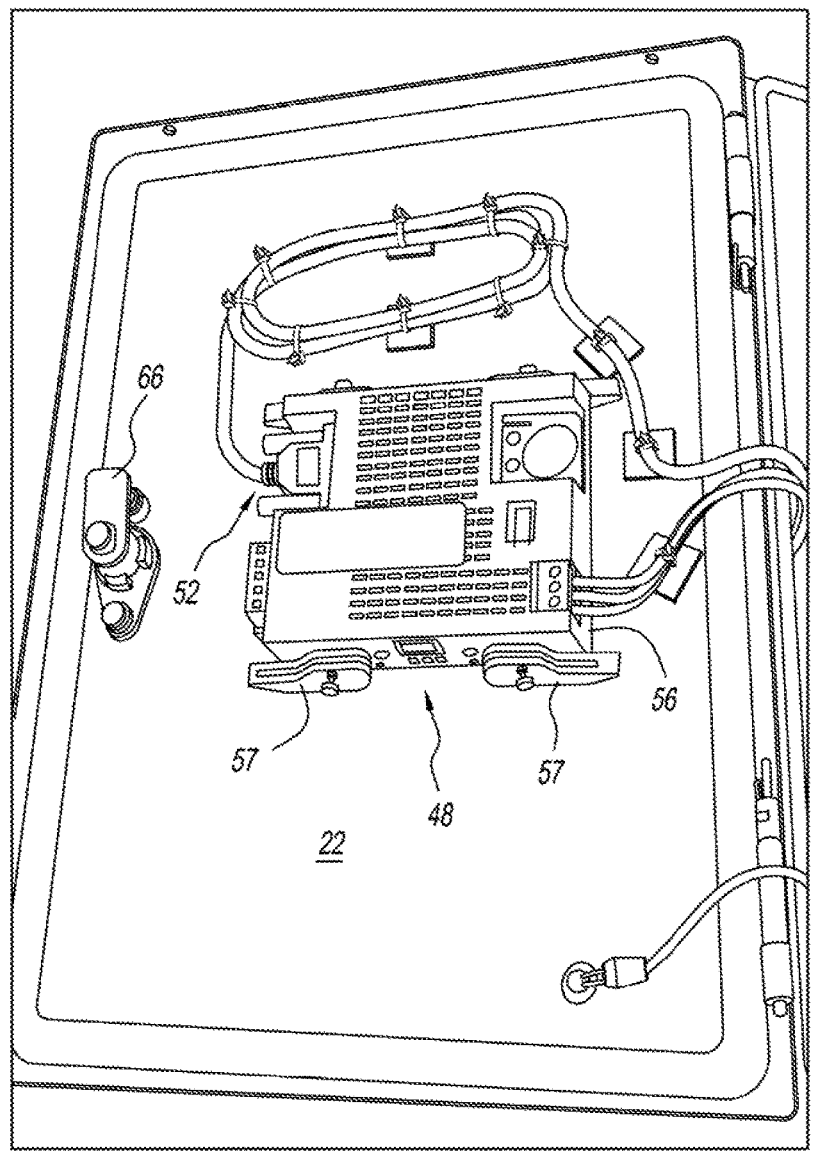
FIG. 2 is a rear view of the rear face of the controller housing, showing the input device mounted thereon.

As shown in FIG. 2, the door 18 is hingedly coupled to the base 14, and is movable between a closed position as shown in FIG. 1 and an open position, as shown in FIG. 2. A display panel assembly 26 is mounted into the door 18, so that the touch screen display 30 of the display panel assembly 26 of the device 10 is visible from the exterior 20 of the door 18 as shown in FIG. 1. The interior components of the display panel assembly 26 including the wiring and plugs are disposed adjacent to in the interior surface 22 of the door 18 as shown in FIG. 2.

The display device 26 includes a TV like or computer like small display panel 30 that preferably includes a touch screen feature that operates in a manner very similarly to the manner in which a touch screen operates on either a Smartphone or a touch screen computer display. One example of a display panel assembly 26 that will work with the present invention is a C400 display device that is manufactured by Allen Bradley-Corporation. The C400 display device 26 shown in FIGS. 1 and 2 has four function bullous. F1 34, F2 36, F3 40 and F4 42, that are disposed on the exteriorly disposed frame 32 of the display panel 26, adjacent to the display screen 30.

Figure 3:
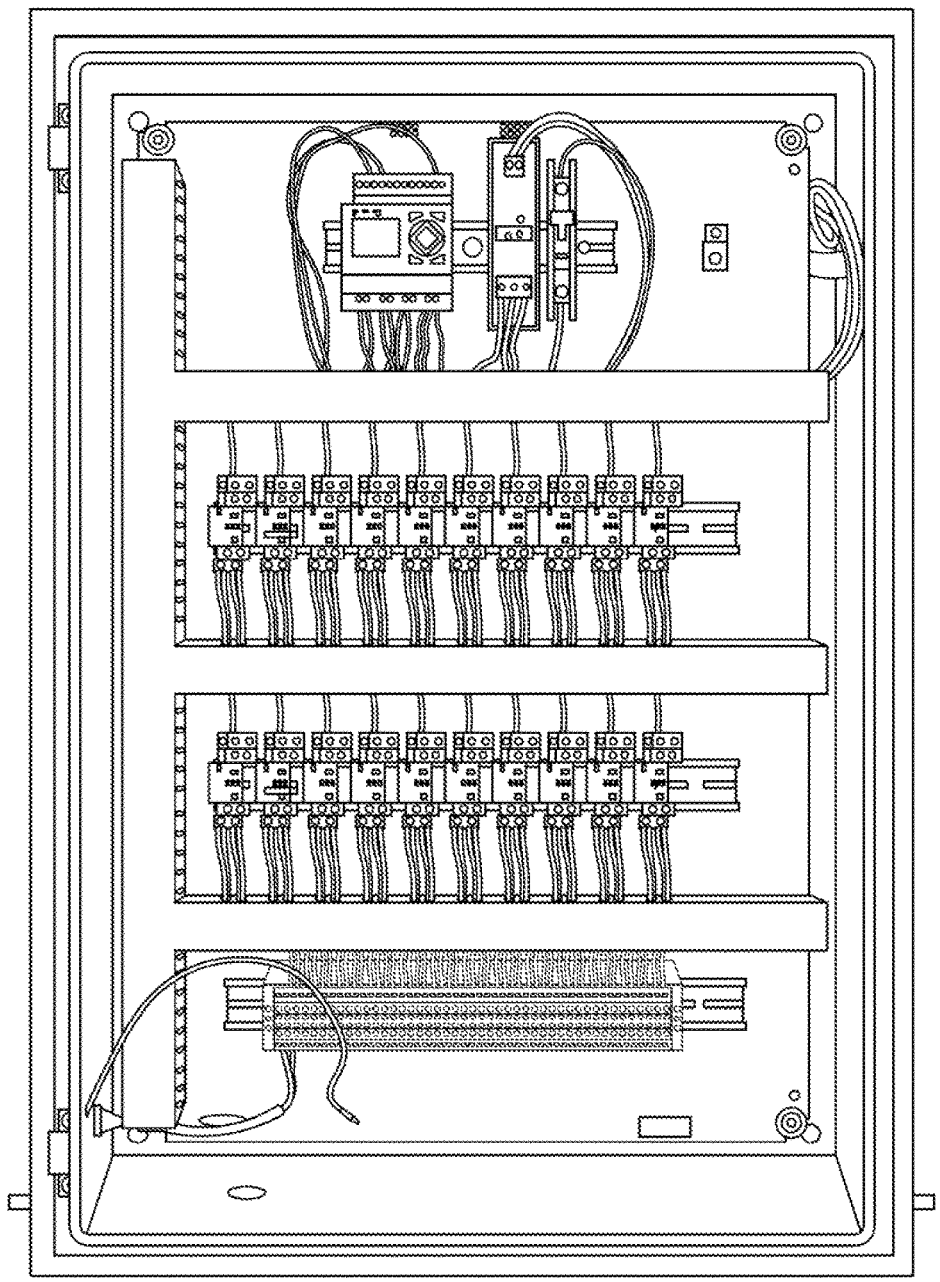
FIG. 3 is a front view of the circuitry contained on the interior of the housing of the present invention.

A locking mechanism 60 that is key actuated, though the insertion of a key (not shown) into a key receiver 62. The locking mechanism 60 is coupled to the door 18 and is movable between a locked and an unlocked position. When in the unlocked position, the user can gain access to the interior of the controller box 14. When in the closed or locked position, the user is unable to gain access to the interior of the controller box housing 14. In lieu of a key actuated lock mechanism, a key pad, key card, dongle or retinal recognition, fingerprint recognition or locking system can be employed The interior of the housing 14 is best shown in FIGS. 2 and 3, with FIG. 2 showing the interior surface 22 the front door panel and FIG. 3 showing the interior of the base member 16. The interior surface 22 of the front door panel 18 includes an interior latch mechanism 66 that is a part of the lock. The interior and control units of the display member are also coupled to the interior surface of the housing box 14. An aperture is formed within the front panel into which the display panel assembly 26 is mounted.

The panel display assembly 26 has a front cover frame 32 having perimetral dimensions that are greater than the size of the aperture formed in the front door 18, so that the panel display 26 frame 32 completely covers the aperture of the door. However, the interior body 48 of the display panel member may have a size that is generally the same size or smaller than the aperture, so that the user can front mount the display assembly 26 to the door 18, by pushing the body 48 of the display panel assembly 26 through the aperture, so that the frame 32 of the display panel covers the hole, whereas the interior body 48 extends through the aperture in the front door 18.

Locking nuts 57 are coupled to the rear body of the display panel device and are engageable with the interior surface 22 of the door 18 of the control panel housing 14 to maintain the display panel body 48 within its proper position within the aperture that is formed on the front door 18.

The panel display includes one or more communication ports 52, 56. These communication pons are capable of receiving wires or other conduits, and are connected to other components that are disposed within the interior of the housing 14 as shown in FIG. 3. Among the components with which the display panel assembly 26 communicates are the various elements of the internal processor and the circuitry of the controller, so that the information can be transferred between the internal processor, circuitry and controller, and also the processor display 26, and also between the processor display 26 and the thermocouple 84.

Figure 4:
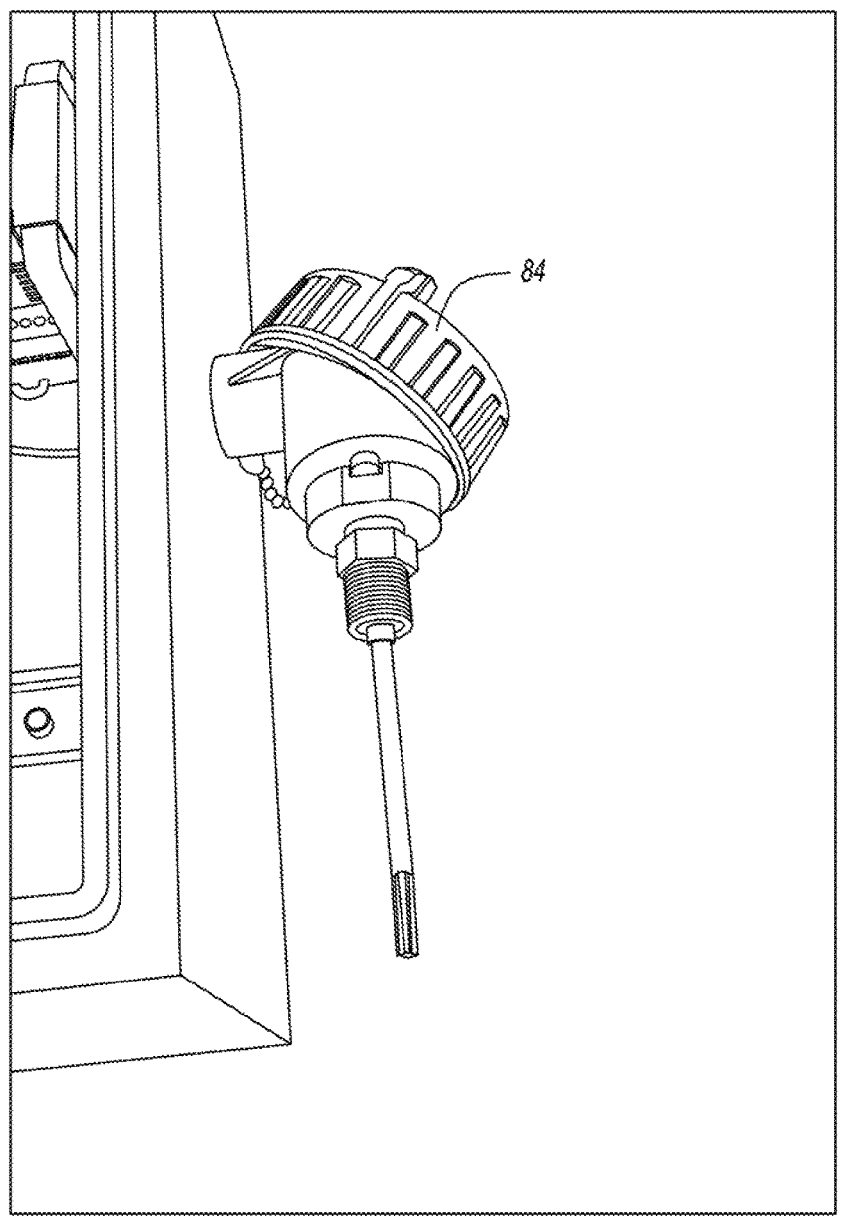
FIG. 4 is a side view of an external temperature probe used in connection with the present invention.

Various internal components that are housed within the interior of the base portion 16 of the controller 10 are shown in FIGS. 3 and 4.

The primary driver of the controller 10 is the programmable logic controller 72. The programmable logic controller 72 comprises a small computer that can be programmed to detect inputs, process data and execute output steps. An example of a controller 72 that will work in connection with the present invention is a Bradley Micro 830 programmable logic controller.

The logic controller 72 includes a plurality of output ports 76 and common ports. The output ports 76 are disposed near the bottom of the device 72 and are close to the communication wire between the conductor 85 that extends between the controller 72, and the thermocouple 84. This conduit 85 couples the thermocouple 84 to a thermocouple card 86 that is a processing card that is operably coupled to the digital controller 72. The thermocouple card 86 is especially designed to enable the Micro 380 digital logic controller 72 to communicate with the temperature sensor, such as thermocouple 84, and to understand the temperature being sensed by the thermocouple 84. The thermocouple 84 is an electronic thermometer, that is designed to detect the ambient temperature in the area adjacent to the thermocouple's probe.

Preferably, the control box 10 is placed near to the place where the vehicle is parked so that the ambient temperature sensed by the thermocouple 84 will reflect the ambient temperature of the environment in which the bus or other commercial vehicle is being parked.

Although the controller includes a plurality of available input ports, none of the input ports are being connected in this particular device. A gray cable exists that is shown that is in communication between the display panel assembly member 26 and the controller 72, so that the controller 72 can communicate with the display panel assembly so that the appropriate display is displayed on the touch screen display and so that inputs to the touch screen display 30 are communicated to the controller 72.

A power supply member 94 is provided for delivering appropriate power to the components and in particular, the main digital controller 72. The main power supply is powered by a 120-volt AC current. This 120-volt AC current is converted to a 24-volt DC output. The 24-volt DC output of the power supply 94 is directed to the primary digital controller 12 that is disposed within the interior of the housing assembly 14. The second place to which the power is directed is the display panel assembly 26 that is disposed on the door panel member 18 of the housing assembly 14.

In addition to the thermocouple card 86, the primary processor 72 also includes a timer, such as timer-counter-memory card 98. The timer-counter-memory card 98 provides the date and time to the controller 72 and receives information from the display assembly 26. This information received from the display assembly 26 is stored for controlling the operations of the controller.

The stored information and received information within the timer-counter-memory card 98 is communicated with the controller 72, so that the device 10 knows what times that the device should be actuated to deliver current to the engine heating device and what time the current should be interrupted between the current source and the block heating devices, so that current is no longer supplied to the heating devices.

A junction box 100 is disposed between the power supply 94 and the controller 72. The junction box 100 includes a plurality of terminals to which the various wires are attached.

A junction box 100 need not be employed, as the wires can be connected through old fashioned wire nuts. However, the junction box 100 couples the wires together in an appropriate manner that is more permanent, durable and neat than the use of a plurality of stray wires held together by wire nuts.

A plurality of outlet switches, including first outlet switch 106 and second outlet switch 108 are also disposed within the interior of the base of the housing assembly 12. The outlet switches 106, 108 are known in the electrical trade as four pole contactors.

Although an infinite number of contactor-type switches can be employed, the controller 10 of the present invention only employs a pair of four outlet controlling switches 106, 108, since the controller 10 is designed for controlling eight outlets.

As also mentioned above, the current draw that is required to operate the heating devices used in conjunction with the present invention makes it advisable to ran each outlet (and hence each device, or set of devices for a single vehicle), off of its own circuit breaker. Therefore, the four input pons 112, 114, 116, and 118 of the four outlets 106, 108 will each have an input wire preferably from a single circuit breaker. Thus, if all four inputs 112, 114, 116, 118 are filled, one is receiving power front four circuit breakers (not shown) so that one can have output to four different outlets (not shown).

The outlet ports 126, 128, 130, 132 can each be coupled to an output wire. Each of the output wires is directed to a single outlet to which a single plug would be used to plug in a single vehicle. Depending upon the amperage draw, it is possible that the outlet might include multiple plugs, to draw or provide a current source for the multiple heaters, such as a block heater, oil reservoir heater, coolant reservoir heater and fuel heater for a particular single vehicle.

The Applicant employs the four pole connectors in the most preferred embodiment because the Applicant found that it is most efficient to couple four outlets together, so that four outlets can be programmed to do essentially the same thing, for four different vehicles. However, the pair of four pole outlets 106, 108 can be programmed differently to accommodate different vehicles or different schedules.

Returning now to the example of the school bus, the first four outlets that are coupled to first output connector 106 can be used for school buses that are used "normally," wherein the buses have a morning route and an afternoon route, and then are parked for the night at about 6:00 p.m. These "normal" bases are shown in Zones 2, 3 and 4 of FIG. 1B. Since these buses are parked for a 12-hour period between 6:00 p.m. and 6:00 a.m., and are parked at 6:00 p.m. on Friday and kept parked until 6:00 a.m. on Monday, one might program the first output block 106 to only provide six hours of power that would be directed from Midnight to 6:00 a.m. on Monday morning through Friday morning, and to otherwise not provide any current or power the rest of the time. Because of the morning and evening routes, such outlets may also be programmed to allow current to flow to the school buses Monday through Friday between 10:00 a.m. and 2:00 p.m. so that the bus's engine block is kept warm between morning and evening routes.

In contrast, the second output block 108 could be programmed to accommodate the needs of special events buses such as those of Zone 266 of FIG. 1B. As such, the devices could be designed to cause electricity to flow to the buses between 6:00 p.m. and 8:00 p.m. on Friday night, when the buses may be parked between their afternoon routes, and the time when they are restarted to perform an evening special events detail, such as transporting students to a football game or basketball game. Additionally, the second output block 108 may be programmed to work between 2:00 a.m. and 8:00 a.m. on Saturday morning, so that the heating device will heat the buses' fluid above the set point when the bus is used for weekend activities such as Saturday basketball games, wrestling meets and the like.

Although a variety of power supplies can serve as power supply 94, a particularly advantageous model is a Sola Power Supply, Model No. SDP06-24-102 that is $^{115}/_{230}$ VAC 04/0.25 A 50-60 HZ Model. The switches are Allen Bradley four pull contactor switches.

Figure 17:
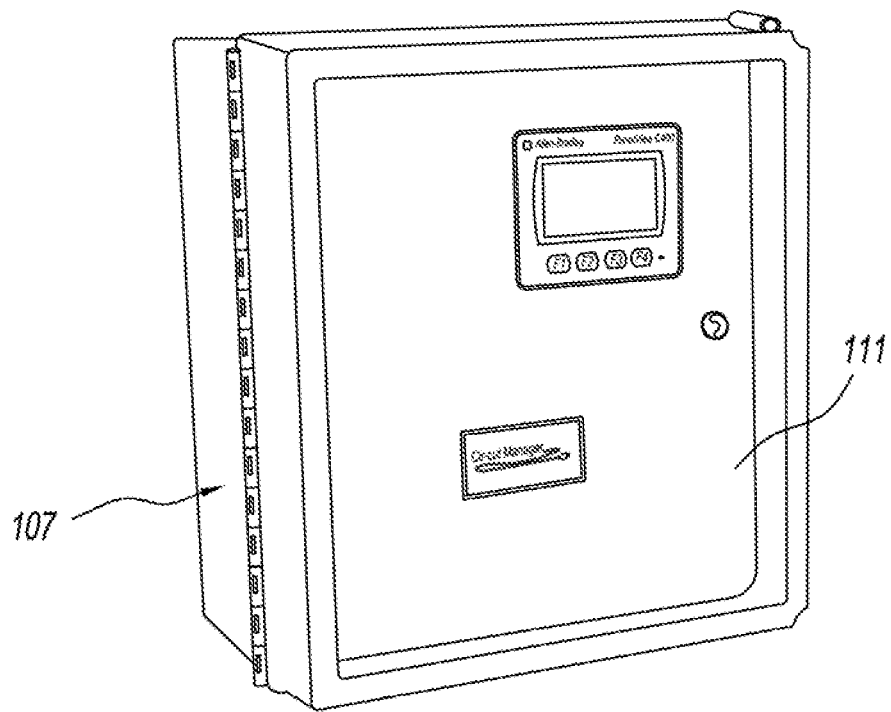
FIG. 17 is a perspective view of a NEMA 4X box which is especially well adapted for use on devices that are positioned in outdoor environments.

The description above generally relates to the indoor version of a panel. A similar panel will work for outdoor uses. Turning now to FIG. 17, a perspective view of a NEMA 4X box 107 is shown that is especially well adapted for use with devices 10 that are positioned in outdoor environments where the device will have to contend with the elements such as rain, wind, snow and dust.

The first modification that is included in box 107 is that box 107 is preferably made to include a thick plastic cover 111 that fits over the panel door. The plastic cover 111 is fitted over the door to provide an extra layer of resistance to moisture, dust and the like, since an outdoor placed panel is more subject to these environmental factors that one placed indoors.

A further modification is to place a heater inside the interior of the housing 12. It has been found by the Applicants that the processor 72 employed with the present invention will generally function at a temperature greater than about 10° F., but will not function well below that temperature. Similarly, the data display 30 will not perform well at temperatures below 0° F. By using a panel heater, such as one available by Allen Bradley, the panel components can be kepi above this temperature so that they will function even if the temperature for example, would reach −20° F. or −30° F.

The operation of the device will now be described to reference to FIG. 5 et seq.

Figure 5:
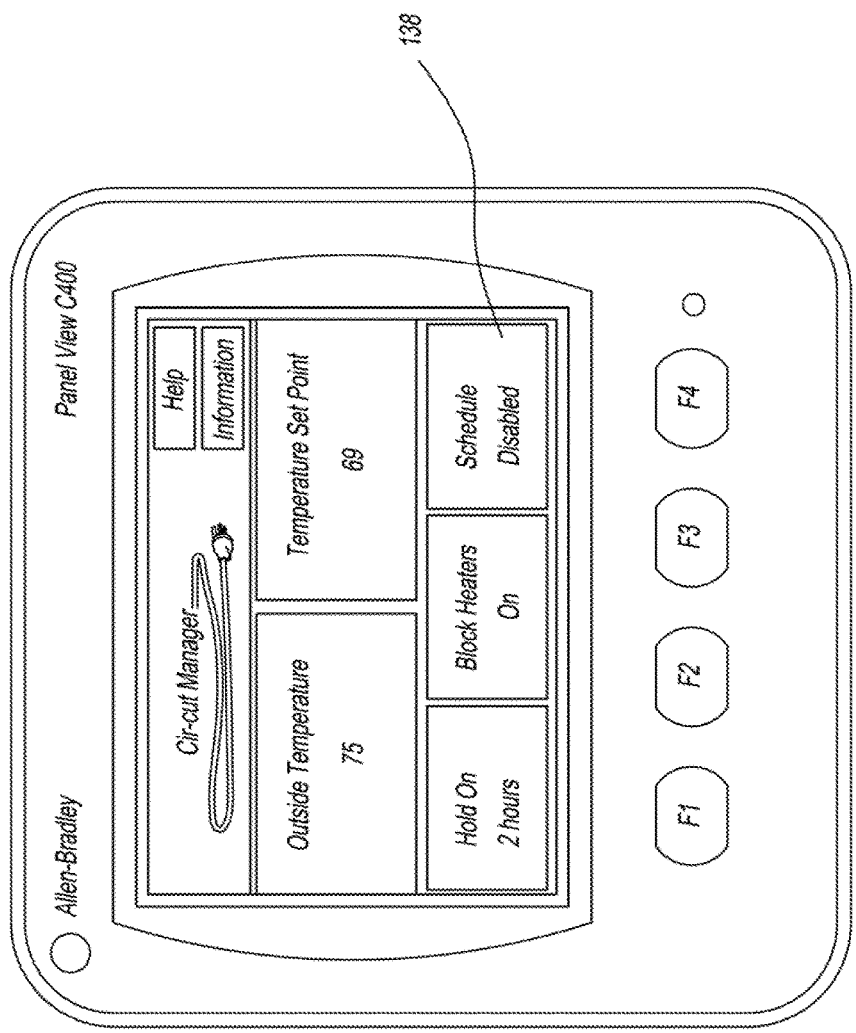

The home screen 138 is shown in FIG. 5. The home screen displays the outside temperature (here, 75° F.) and the temperature set point (here, 69° F.). The outside temperature is derived through a thermocouple 84 that is shown in FIG. 4. As discussed above, the thermocouple 84 is in communication with the processor 72, and feeds information to the processor about the ambient temperature outside the control box 12, that should approximate the ambient temperature of the school buses.

Although the thermocouple 84 is shown as being coupled to the exterior of the base of the control box 12, the thermocouple can be located remotely from the control box. For example, if the control box 12 is placed on an interior surface of an exterior wall of a building, the thermocouple 84 can be placed on the exterior surface of the wall so that the thermocouple 84 measures outside temperature, rather titan the interior temperature of the building.

As a thermocouple 84 and a processor can be coupled either directly by a connector, or wirelessly, it will be appreciated that the distance between the positioning of the thermocouple 84 and the control box 12 can be significant depending upon the particular needs of the system. However, since the control box 10 must also be coupled to outlet wires that lead to outlets positioned adjacent to the places where the vehicles are parked, it is preferable to place the control box housing 12 and thermocouple 84 somewhere close to the places where the vehicles are parked, if for no other reason than to save the costs and trouble of running long wires.

The temperature set point is the predetermined temperature that the user sets on the device to determine the temperature at which the device will, turn on to allow current to flow to the heating devices to heat the vehicles' fluids. For example, if the temperature set point is 25° F., and the outside temperature never falls below 40° F., the device will not allow the heating devices to turn on, because the outside temperature fall below the set point. In this regard, the temperature set point can be viewed as something of a trigger that causes the device to actuate to thereby cause the heating devices to turn on. If the trigger is not actuated, the heating devices will be not operated.

Returning now to the main screen 138, a help button is disposed on the screen. The help button can be actuated on any of the display screens, if the help button screen is actuated, a message will be displayed on the screen that gives the user information about the particular screen, and how to actuate the buttons on the screen, and the need for actuating buttons and operating devices that appear on that screen.

Figure 6:
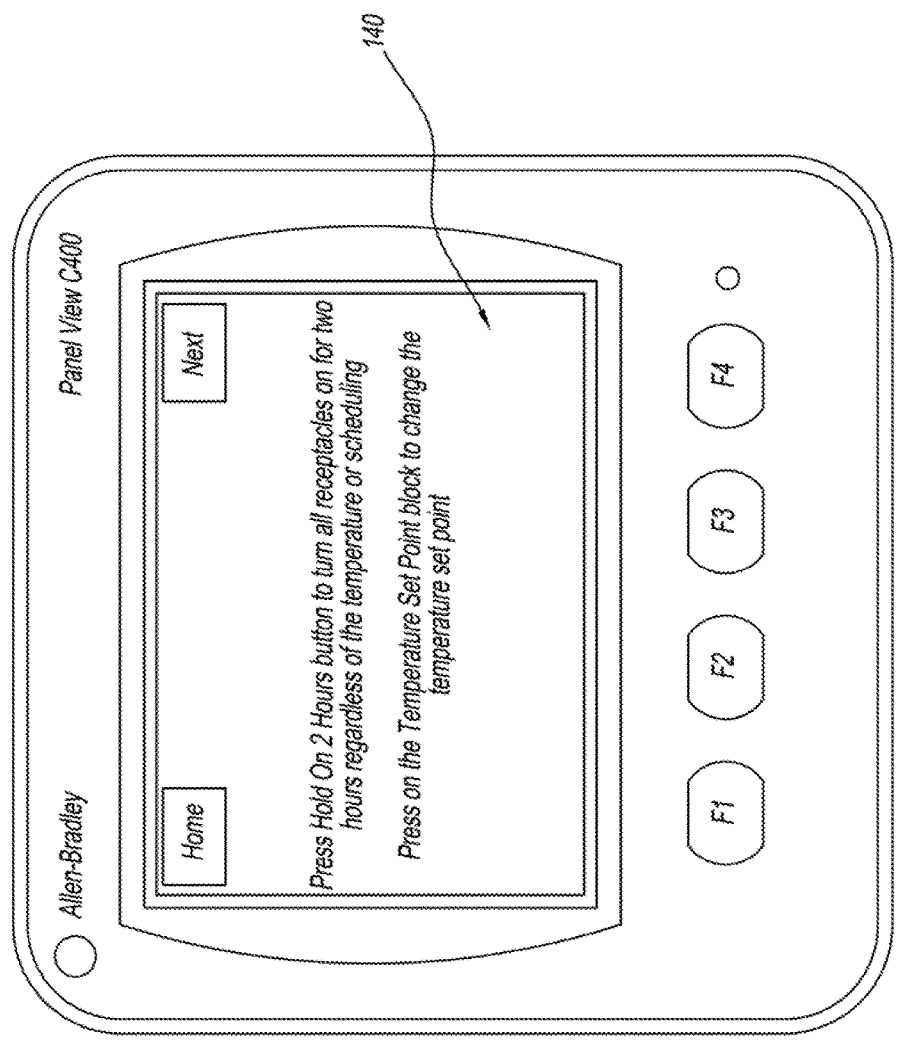
FIG. 6 is a second screen shot display showing the display normally viewed during the actuation of the block heater.

A typical help screen 140 is shown in FIG. 6 of the type that would be displayed if the help button is actuated on the main screen of FIG. 5. Screen 140 states "press hold on two-hour button" to turn on all receptacles for two hours regardless of the temperature or scheduling. Press the temperature set point block to change the temperature set point.

This screen 140 explains that the "hold on" button will serve as something of an override button that will turn the device an for a two-hour period to thereby override the timing function of the device. The hold button may advantageously be used in conjunction with a vehicle that not being used for a special occasion. For example, if several buses were being employed on a special event that occurred over a weekend, the fleet operator might wish to employ the "hold on button" to turn on a heating device that was coupled to a bus that was on the regular schedule, so that the regular schedule would be over-ridden and the heating devices would begin to heat the regular schedule busses to an appropriate temperature, so that the fluids of the particular "regular schedule" bus would be warm enough to permit the bus to start easily if it were necessary to use the regular schedule bus to replace a special event bus that broke down or became otherwise disabled.

Pressing the "hold on" button causes the processor to actuate all of the circuits to allow current to flow through all of the circuits to the various outlets coupled to all of the basis vehicles.

Another time when the "hold on" button is useful if an auxiliary electrical device needs to be employed in connection with a vehicle. For example, even if during the summer, the battery on a particular bus goes dead, the "hold on" for two hours button can supply electricity to the outlet near the particular bus so that a battery charger can be plugged in and provide energy to the needed battery. Similarly, if a mechanic is operating an electrical tool to make a repair on the bus in the parking lot, the hold on burton can be pushed so that the mechanic will have a source of power to operate his tool for a two-hour period.

It should also be noted that the time period for the "hold on" feature is variable by the user. As such, the user can vary the hold on feature for a short period of time, such as 15 minutes or 30 minutes to a longer period of time such as several hours. This variability is helpful and useful at times when the temperature is above the set point, or a particular event is occurring. For example, if the hypothetical mechanic will only need his tools for a short period of time, he can set the hold on button to 45 minutes, which may give him ample time to perform his repairs without wasting electricity by having electricity supplied to the bus for a longer, two or four-hour period.

Additionally, if a bus parking lot is being used for an event such as a festival that is run for a six or eight-hour period of time, the hold on button can be used to provide power to the outlets that can be used by the various festival rides and games and lighting operators during the duration of the festival. This feature might be especially useful when running outdoor lights as a part of the festival, as one might want the lights to be on all night, or during the festival operating hours.

Another feature of the present invention is the fact that the hold on feature enables the device to "time out" the electricity at a desired time. For example, if one were having a festival in the bus parking lot that extended between 8:00 p.m. and Midnight, and if one wanted to leave when the festival was over at Midnight, one might use the hold on button to keep the lights on until 2:00 a.m. or 3:00 a.m., so that the area would be lit for a period of time that was sufficient to enable festival operators and workers to clean up and all the festival guests to exit the area.

It will be noted that the main display screen is a block heater on button that is shown as being lit in green in main display 138. The block heater on button is not an actuable burton but rather a display area. The display area of the block on button indicates that the current state of the operation of the device.

As shown in FIG. 5, the main display screen 138 shows the block heater being lit. This provides a visual and textual indicator to the operator that the block heaters are on and that current is getting supplied to the outlets, and that the controller device 10 is allowing current to be supplied to the outlets so that the outlets are live. At times when the controller 72 is not allowing current to flow to the outlets, and therefore the block heaters are off, the green display shown in FIG. 5 would turn into a red display so that one could visually and quickly know that the heaters were off at that time.

Although there is no requirement that any particular color be used to indicate any particular operating condition or the use of two different colors is a valuable feature insofar as it allows the operator to determine the status of the block heaters at a distance that is likely greater than the distance at which the user would be able to read the textual message on the screen.

Another button present on the display screen 138 of FIG. 5 is the information button. The information button can be programmed to take the user to another screen, to display whatever information the programmer or user desires. For example, the information that may be displayed upon pushing the information button could include information about the emergency maintenance person's phone number, address or other pertinent information such as emergency phone numbers that should be called in the case of an emergency. Additionally, information such as emergency shut off information could be displayed so that in case of an emergency, the user would know how to shut power down to thereby prevent any problems from being exacerbated, or to shut the system down in the case of a fire, gas leak or the like.

Returning now to FIG. 6 it will be noted that the help screen 140 also includes a "home" and "next" button. The home button takes the user back to the initial display screen 138. The next button takes the user to the next display screen in a sequence. Due to the somewhat small size of the display (as compared to a computer screen), it might be useful to provide the need help information over a series of screens, as it may not fit on a single screen.

Figure 7:
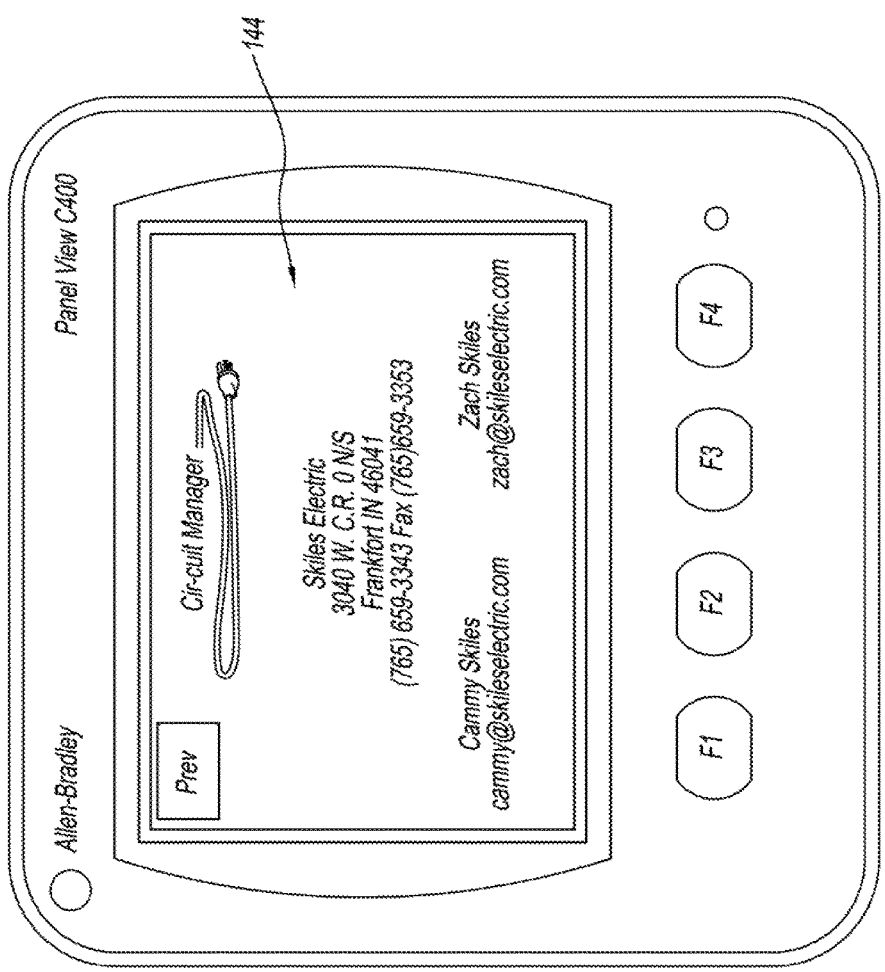
FIG. 7 is a screen shot view of the information screen, that provides information about the manufacturer of the device and contact information therefor.

Turning next to FIG. 7, a sample information screen 144 is shown. In the sample information screen 144, information is provided about the manufacturer of the device. This information is useful, for if a malfunction or emergency occurs, it provides the user with information that enables the user to contact the manufacturer to trouble shoot and or fix the problem. As stated above, the information screen could include other information that the user deems pertinent, and is not limited certainly to information about the manufacturer.

Main screen display 138 also includes an outside temperature and set point display. It will be appreciated that the outside temperature button is basically a display button that cannot be changed manually, as one cannot change the outside temperature manually. As discussed above, the temperature displayed on the outside temperature display is the temperature read by the thermocouple 84. However, the temperature set point button is an actuable button. By pressing the temperature set point button on the touch screen display, the first input screen is shown.

Figure 8:
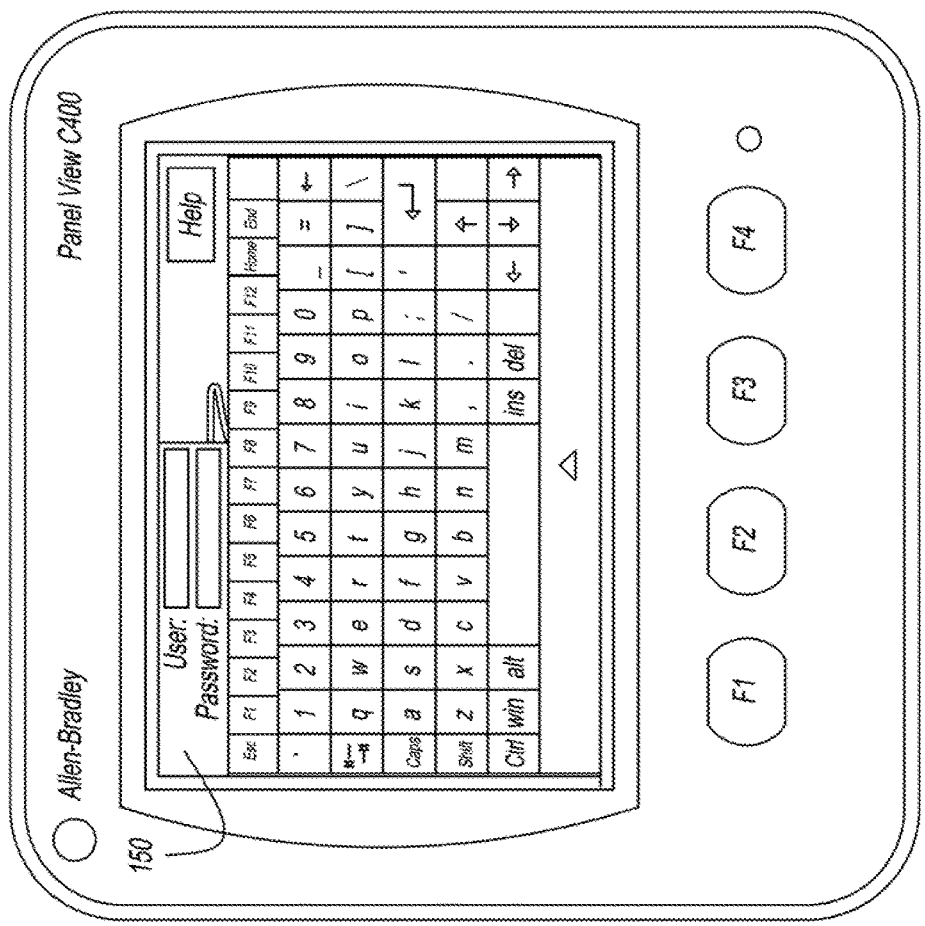
FIG. 8 is a screen shot of a keyboard-like display screen useable to input information into the device.

This temperature input screen 150 is shown in FIG. 8. The first input screen 150 is basically a display of a typewriter keyboard that can be actuated on the touch screen display by touching the appropriate keys on the keyboard to input information into the device 10. This typewriter keyboard display is not that different than one might find on a Smartphone or personal, digital assistant.

For reasons of security, the first input screen that comes up requires the user's name and password are to be typed into the screen, so that the device 10 can determine whether any changes that are being made to the screen are changes that are made by an authorized party. More importantly, the use of a user name and password are required to ensure that changes made are not made by an unauthorized party.

The touch screen is preferably pressure activated, rather than capacitance actuated, as a pressure activated screen is more easily useable with either gloved hands or with a stylist type device.

Since one of the purposes of the device is to operate block heaters for keeping commercial diesel engines warm enough to start in arctic-like conditions, the device will often be used under cold conditions. Under cold temperature conditions, it is likely that the users will be wearing gloves that often do not work well with a capacitance-type screen. Additionally, because of the small size of the display, the keys will necessarily also be small sized and as such, may better be actuated with a thin pressure inducing stylist rather than a finger that, because of its width, will often make it difficult for the user to strike the appropriate key.

Figure 9:
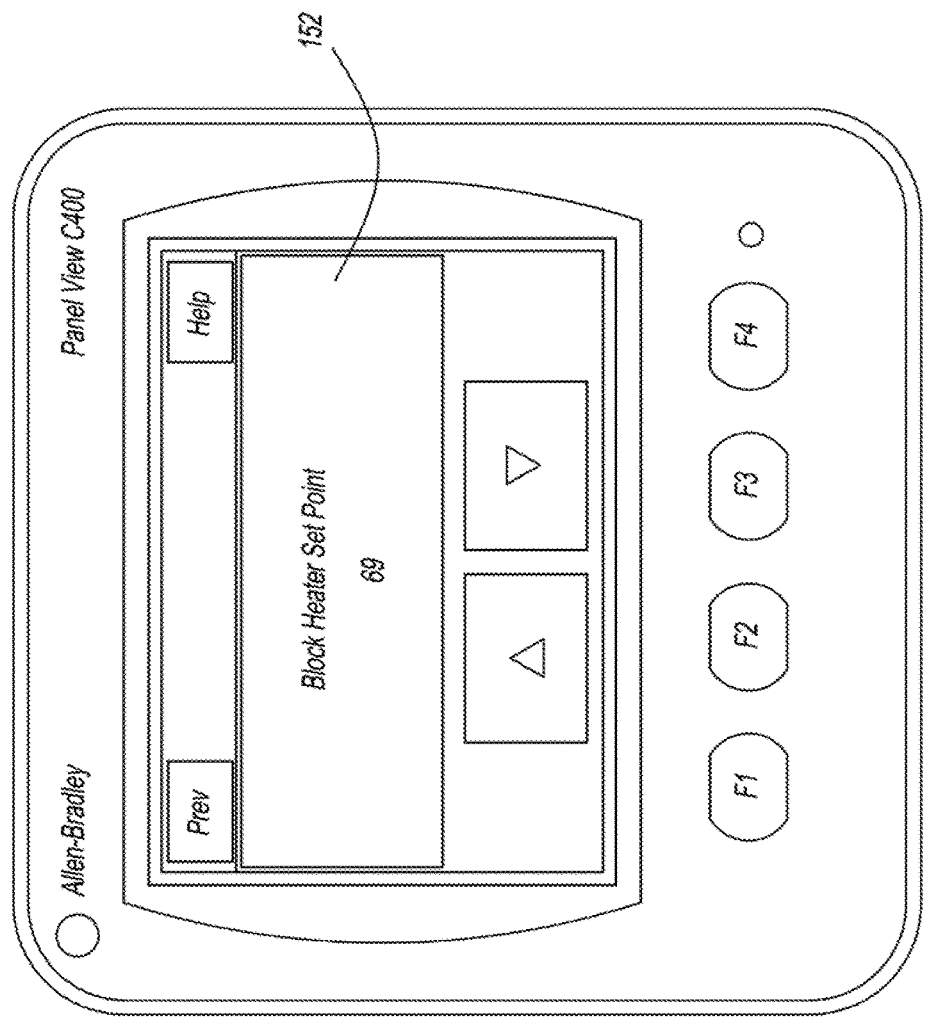
FIG. 9 is a screen shot view of the set point heater adjustment display.

Once the user's name and password are input on the keyboard screen 150 of FIG. 8, the block heater set point screen 152 of FIG. 9 is shown to the user. One can use the up and down buttons on the block heater set point screen 152 to raise or lower the block heater set point(s) to an appropriate temperature. Although it is envisioned that a particular pre-determined set point, such as 25° F. will be chosen, the ability of the set point to be varied helps to give the user additional flexibility to set the device at an appropriate set point temperature that at best matches his climatic conditions of the particular user's environment, and the equipment needs of the particular user.

For example, a user in the more southerly cold areas (e.g. Kentucky) may employ oils in his equipment that are normally thicker and more viscous than the oils employed by someone in the far north climate (e.g. Manitoba). Because of the different viscosity properties of these oils, the user may wish to set the set point at 30° F. rather than 25° F., as the oil in his equipment may make staring below 30° F. as difficult as starting at 25° F. would be for equipment with a thinner, less viscous oil.

Once one has entered an appropriate set point on the set point screen 152, one can then go back to the main screen 138 and actuate the schedule enabling disabling button. Pressing the scheduling disabling button will take one to the keyboard screen 150, if the scheduling disabling button is the first button hit after the device has been dormant for a sufficiently long period time that the device has reverted back into the "lock" mode wherein a user name and password are required to make changes to it.

At the input screen 150 of FIG. 8, one would then enter one's user name and password in a manner similar to the manner described above in connection with the adjustment of the heater block set point. However, assuming that the identification step is passed, the user will be taken to the scheduling display screen 156 shown at FIG. 10.

Figure 10:
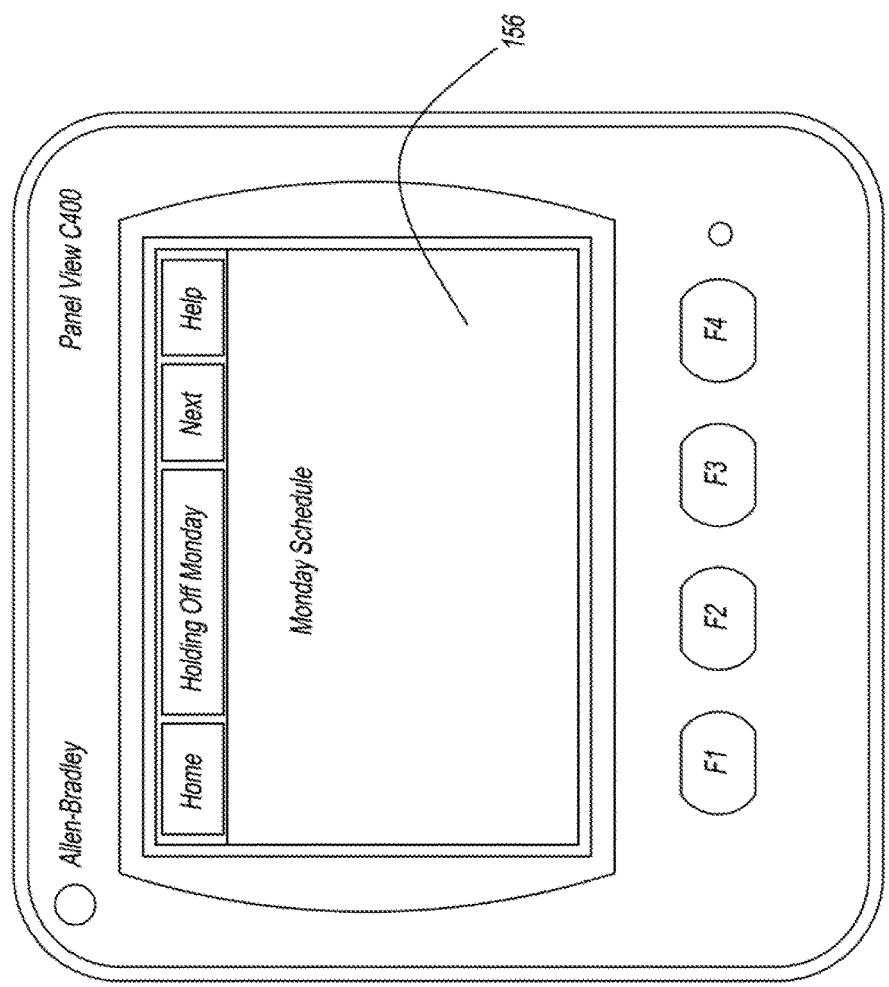
FIG. 10 is a screen shot of the schedule display of the present invention.

Display screen 156 of FIG. 10 shows "Monday's Schedule". The device 10 is currently designed so that the schedule for the device is established on a day-by-day basis. A day-by-day basis is preferred because it is likely that the usage of the devices will change on a daily basis. With many operations, the controller 10 will have a first schedule that will exist during the weekdays, and another schedule that will work on weekends, or other "days off". However, because the operations of all various businesses are different, it is important for the device to have the flexibility and capability to establish a different schedule every day, regardless of that different day as a Sunday or Tuesday, or the equipment day off is a Monday or Saturday.

The buttons along the top of the display screen 150 include a home button that takes the user back to the main screen 138 of FIG. 5. The next button is highlighted in "holding off Monday". This second button is a status button. When the device is in this "holding off Monday" mode, it takes Monday off the schedule.

When the device is "off the schedule", the device operates in the following manner. First, the holding off schedule has no bearing if the schedule is not enabled. If the schedule is not enabled, the device goes into its default mode to keep the current flowing through the device and to the outlets on a 2-4 hour, seven day a week basis.

However, assuming that the schedule has been enabled, the device when placed in a "holding off mode" will cause the device to place the heaters in a "off position", so that no current flows to the outlet through the day. For example, in the bus fleet operation disclosed above, Saturday and Sunday might be placed in the "holding off" position, since one would not need to run the block heaters on a Saturday or Sunday, since the buses were not being operated on a Saturday or Sunday. Nonetheless, since the block heaters were being operated on Monday through Friday, Monday through Friday would not be placed in the "hold off" configuration.

The help button takes one to a help screen that is specifically designed to provide information about the scheduling screen on which the help button was utilized.

The help screen can also provide information to describe the status of the device as currently set. For example, if one were to hit the help screen with the "holding off Monday" mode display being shown, the help screen might include a message that would say something to the effect "Monday is being held off. Therefore, no current will be delivered to the outlets regardless of the temperature on Monday".

Figure 11:
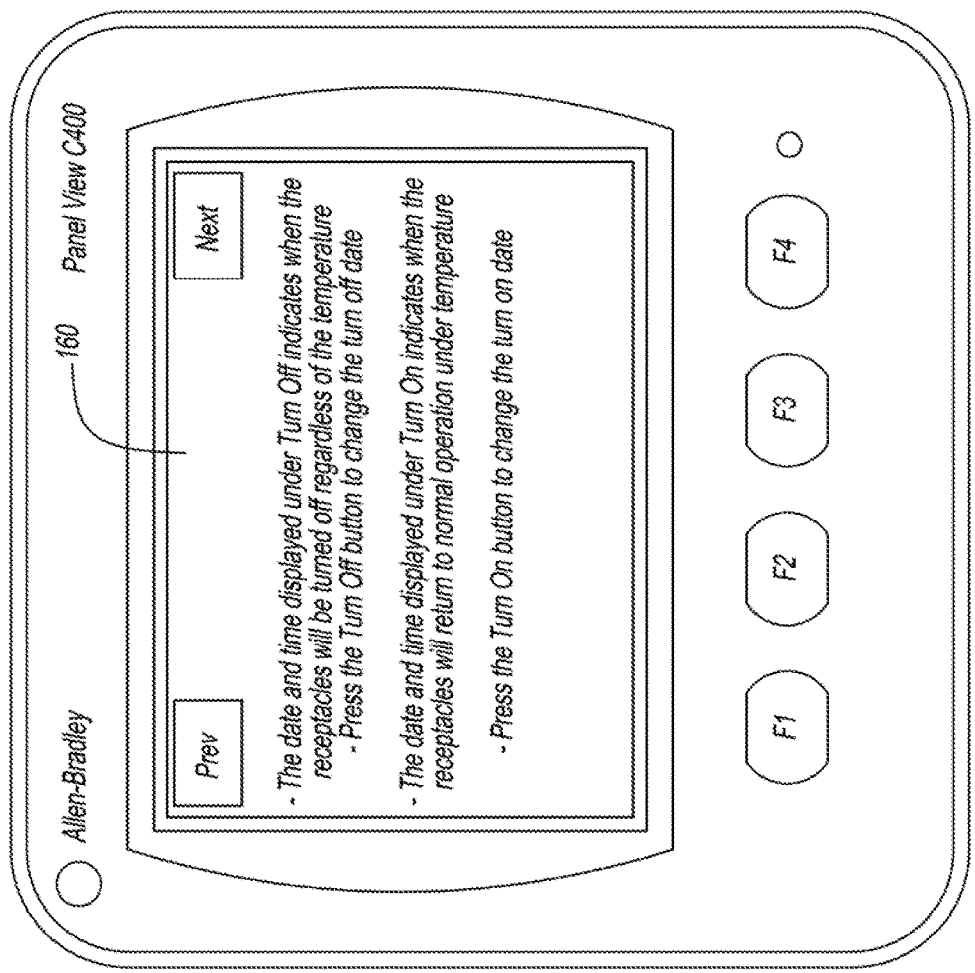
FIG. 11 is another screen shot view of the present invention that provides information about the "turn off time" representing the point at which the block heaters are turned off.

Alternately, a more generic information display can be given, such as shown on the display screen 160 of FIG. 11. The display screen shown on FIG. 11 gives generic information about the scheduling button, its operation, and how to adjust the parameters thereon so as to achieve the result desired by the user.

Returning back to the scheduling screen 156 at FIG. 10, the operation of these scheduling screen 156 to enact a schedule for Monday will now be disclosed.

Figure 12:
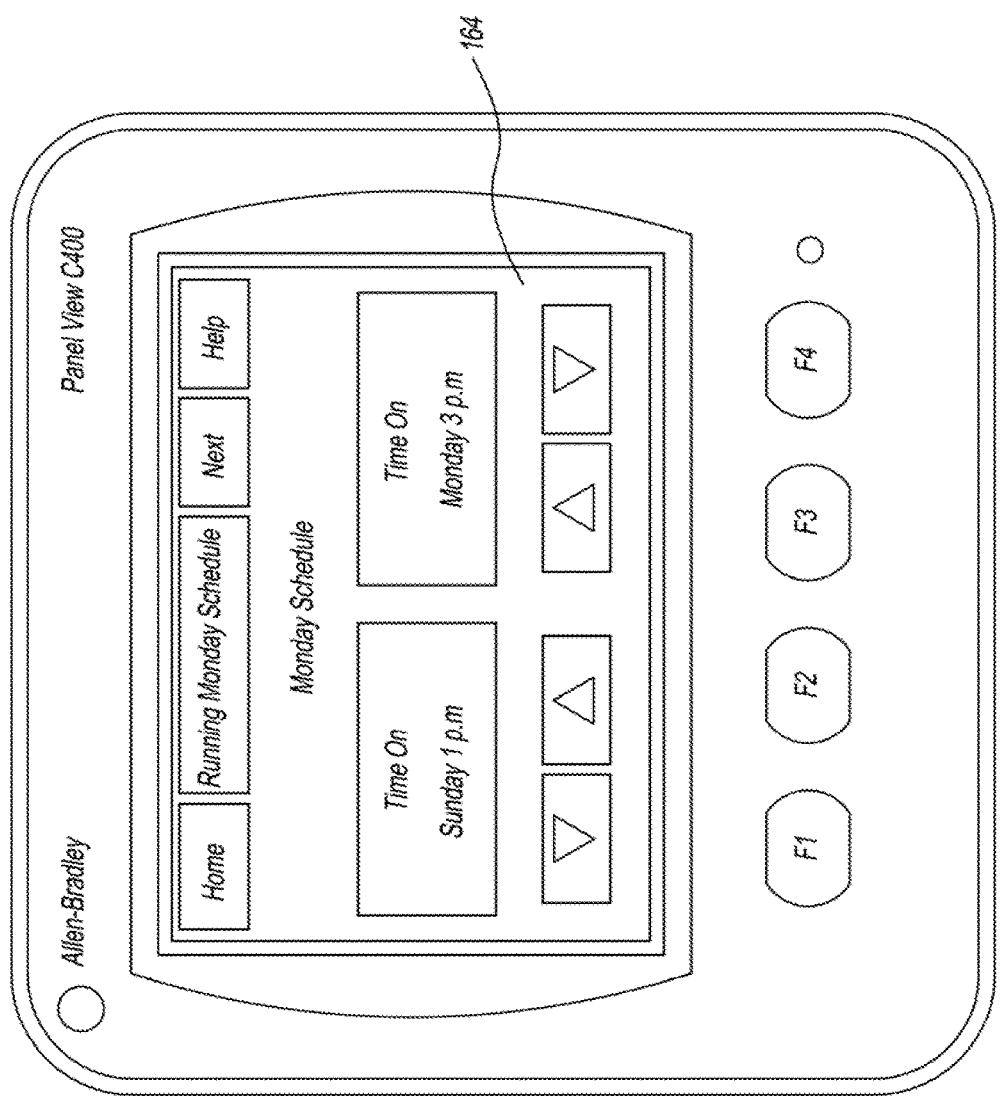
FIG. 12 is a block heater "turn on", block heater "turn off" timing input screen.

In order to make a change or to establish a Monday schedule, the first thing that one does is to press the "holding off Monday" button. Turning now to FIG. 12, the holding off Monday button will change the device to display a display 164 shown in FIG. 12. Alternately, the display screen shown in FIG. 12 can be reached by hitting the next button on the schedule display screen 156.

When the display screen 164 of FIG. 12 is actuated, one will see the display screen with a time on and a time off. This "time on", "time off" can then be adjusted upwardly or downwardly (or forwardly or backwardly) through the arrow button shown on the screen.

The "time on" represents the time when the device is actuated so that the device will allow current to flow to the buses if the thermocouple detects a temperature that is at or below the set point. The "time off" button will cause the device to stop the flow of current to the outlet, regardless of the set point position.

As discussed above, the decision to actuate the unit to allow current to flow to the block heater is dependent upon both on the device being actuated to allow current to flow, and the set point being below a certain level. For example, if the Monday schedule states that the Time On is midnight, and that the Time Off is 6:00 a.m., a reading of the temperature by the thermocouple 84 at midnight of 37° F. that was above the 25° F. set point, would cause the device not to allow current to flow to the outlet and to keep the block heaters in a "turned off" mode. The block heaters would be turned off because the temperature was not cold enough to require the use of the block heaters.

However, if the temperature dropped at 2:00 a.m. below the set point, the fact that the set point had been achieved during the window of operation of the device would cause the device to "turn on" to thereby allow current to be delivered from the current source to the outlet, and thereby, to the engine heating devices, so that the heating devices could turn on and help to warm up the vehicle. Similarly, if the temperature at 4:00 a.m. has risen above the set point, the rise in temperature sensed by the thermocouple and transmitted to the controller might cause the controller 72 to turn the device 10 off, so that current was no longer allowed to flow to the block heating devices, to thereby save electricity.

From the screen, it will be noted that there is generally one time that one can set for any particular day. This however is not the case. The device can be programmed so that one can have multiple on and off times. Nonetheless, for most business and commercial applications, the Applicants have found that one on/off time will suffice in most cases. As discussed above in connection with the bus situation, it might be expected that one might desire to have the block heaters operational not only between midnight and 6:00 a.m. before the buses first shift, but also between 10:00 a.m. and 2:00 p.m. between the morning and afternoon shifts.

Figure 13:
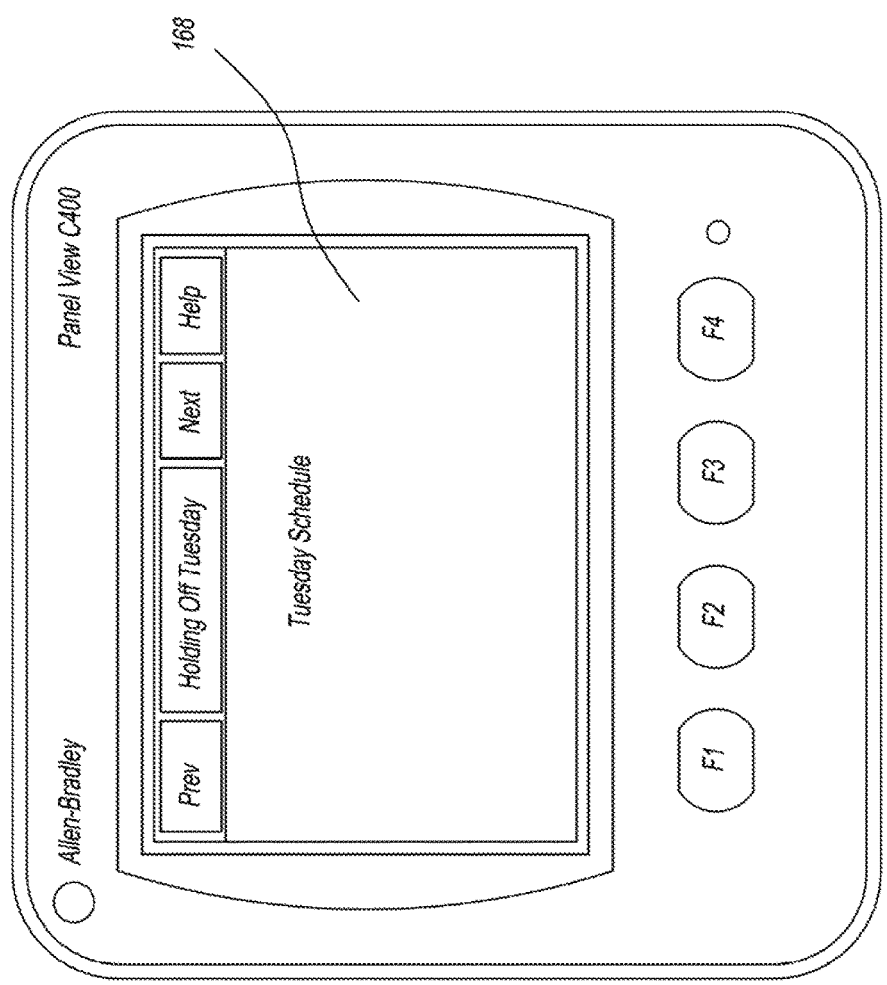
FIG. 13 is a Tuesday schedule display screen.

Turning now to FIG. 13, it will be noted that pressing the next "end button" after the schedule has been set for Monday, will enable one, as shown on the Tuesday display 168 to set Tuesday's display. Tuesday's schedule is set in a manner very similar to the manner in which Monday's schedule was set. One option that is provided with the device is to enable the user to choose between which of the plurality (here two 106, 108) of outlet switches 106, 108 are actuated during any particular schedule.

As discussed above, each of the various outlet switches 106, 108 is capable of controlling four outlets. The outlet switches 106, 108 are individually controllable such that the first outlet switch 106 (and its controlled outlets) can be on a schedule that is entirely different from the four outlets controlled by second outlet switch 108. Returning back to the hypothetical school bus situation, one can use the first outlet switch 106 to set a schedule that accommodates buses that are not used for special events, but are only used for morning and evening runs, and sit idle through the weekend. In contrast, the second outlet switch 108 can be employed to be coupled to special event buses, that are used on the weekend, so that the block heaters will be turned on during certain weekend times to ensure that the buses are operational during the weekend.

Figure 14:
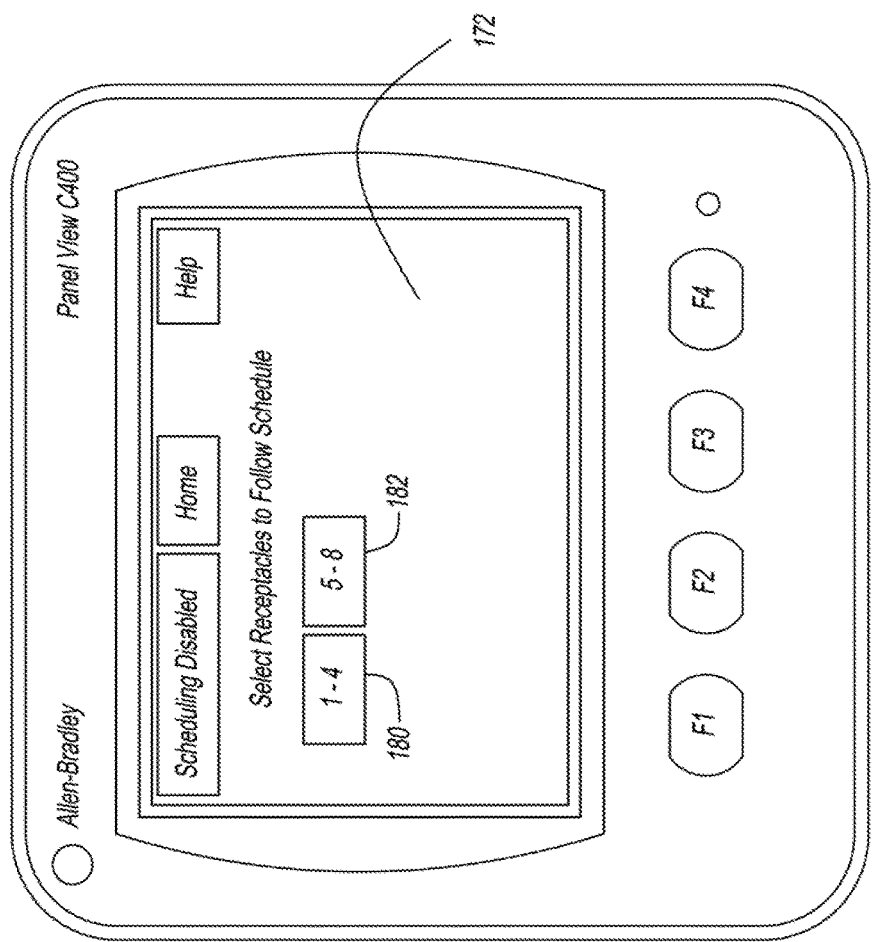
FIG. 14 is a display screen showing various receptacles operated by the controller.
Figure 15:
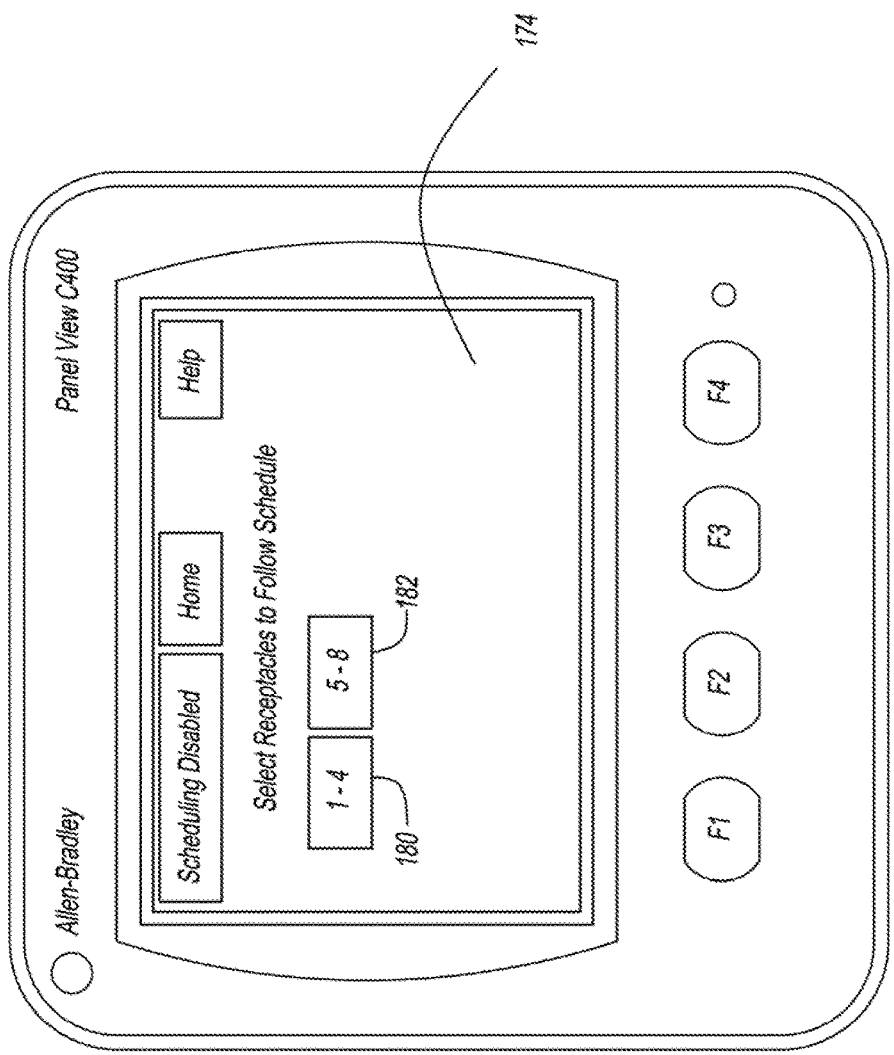
FIG. 15 is a display screen similar to FIG. 14, showing that both receptacles are actuated to follow the input schedule.
Figure 16:
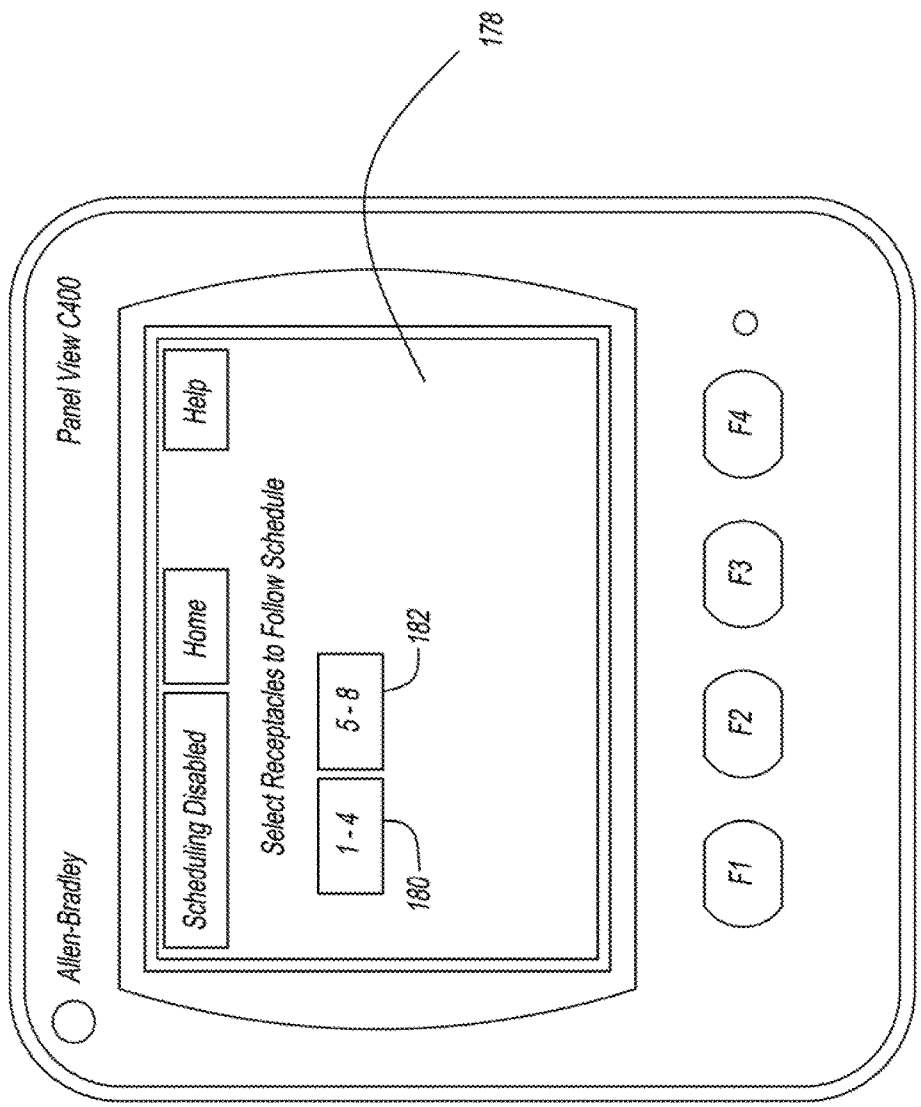
FIG. 16 is a display screen, similar to FIG. 15, except showing that only one of the two receptacles has been activated by the controller of the present invention.

To illustrate this variability, a first receptacle actuation screen 172 is shown in FIG. 14, a second receptacle actuation screen 174 is shown in FIG. 15, and a third receptacle actuation screen 178 is shown in FIG. 16. In FIG. 14, both of the switches including first switch 180 and second switch 182 are shown in red, such that neither the first switch 180 nor the second switch 192 is being tied to the schedule that is set up on that particular date.

FIG. 15 shows that the first switch 180 and second switch 182 are also being operated identically. However, in FIG. 15, both the first and second switches 180, 182 are being tied to operate on a schedule that was input into the device.

FIG. 16 shows a situation where although the first switch 180 is actuated to operate according to the schedule that has been programmed into the device, the second switch 182 is not designed to follow that particular schedule. Since the device can accommodate multiple switches, it can also be programmed to put the first and second switches 180, 182 on different schedules.

Having described the invention in detail with respect to certain preferred embodiments, it will be appreciated that variations and modifications exist within the scope and spirit of the present invention, and that the invention is only limited by the prior art.

What is claimed is:

1. A vehicle fluid heating system for achieving an elevated predetermined fluid temperature for at least one fluid of a first and second vehicle during an idle period having a duration defined by a start point and an end point, the hearing system comprising
    a first vehicle fluid heater configured for being coupled to the first vehicle in thermal communication with the first fluid of the first vehicle, and a second vehicle fluid heater configured for being coupled to the second vehicle in thermal communication with the first fluid of the second vehicle,
    at least one temperature sensor for sensing a temperature of a temperature source that has a correlative relationship to the first fluid of the first and second vehicles,
    a settable timer for enabling the user to establish the start point and the end point of the idle period of the first and second vehicle heaters,
    a controller in communication with an electrical source for controlling the flow of electricity from the electrical source to the first and second vehicles fluid heaters, in communication with the temperature sensor for receiving temperature information, and in communication with the settable times for obtaining information about the start point and the end point of the vehicle idle period,
    wherein the controller includes a processor for receiving the temperature information, idle period start point, and idle period end point for determining a vehicle fluid heating interval having a duration less than the duration of the idle period that achieves the elevated predetermined fluid temperature at the end of the idle period and a switch actuator for allowing the flow of electricity from the electrical service to the first and second fluid heaters during the fluid heating interval.

2. The vehicle fluid heating system of claim 1 further comprising an input device for enabling the user to input operational data into the controller, including idle period start point and end point data.

3. The vehicle fluid heating system of claim 1 wherein the timer includes a calendar function for enabling the user to use his input device to input operational data for at least a first day having a first idle period start and end point, and a second day having a second idle period start and end point different from the start point and end point of the first day.

4. The vehicle fluid heating system of claim 3 wherein the heater probe includes an actuator in communication for enabling the user to control the flow of electricity at the site with the first heater probe.

5. The vehicle fluid heating system of claim 4 wherein the actuator comprises at least one of a manually actuated electric flow control switch, an automatically actuated electrical flow control switch and a fluid sensor operatively coupled to an electrically flow control switch.

6. The vehicle fluid heating system of claim 4 further comprising a third vehicle heater probe insertable into a second fluid reservoir of the first vehicle.

7. The vehicle fluid heating system of claim 1 wherein the first vehicle fluid heater comprises a first vehicle heater probe insertable into a fluid reservoir of the first vehicle in contact with the fluid in the first fluid reservoir.

8. The vehicle fluid heating system of claim 1 wherein the temperature sensor comprises a thermos coupler disposed in an area adjacent to at least one of the first and second vehicle for detecting a temperature source comprising an ambient temperature of the area adjacent to the at least one of the first and second vehicles.

9. The vehicle fluid heating system of claim 1 wherein the temperature sensor comprises a temperature sensor in thermal communication with the first fluid of the first vehicle.

10. The vehicle fluid heater system of claim 1 wherein the switch actuator comprises a first switch actuator operatively coupled to the first vehicle fluid heater, and a second switch actuator coupled to the second vehicle fluid heater, wherein the controller and processor are configured for controlling the flow of electricity to the first vehicle fluid heater separately from and independently of the second vehicle fluid heater.

11. The vehicle fluid heating system of claim 10 wherein the controller is configured for determining a first vehicle fluid heating interval for the three first vehicles based upon a first idle period determined from a first idle period start point and end point, and for determining a second vehicle fluid heating interval for the three second vehicles based upon a second idle period determined from a second idle start point and end point, wherein the duration of the first idle period is different from the second idle period.

12. The vehicle fluid heating system of claim 1 wherein the first vehicle comprises at least three first vehicles, each of the three first vehicles having a first vehicle fluid heater and the second vehicle comprises at least three second vehicles, each of the three second vehicles having a second vehicle fluid heater.

13. The vehicle fluid heating system of claim 1, wherein the controller establishes the fluid heating interval by determining the temperature sensed by the sensor, determining the heating interval time period duration necessary to achieve the elevated pre-determined fluid temperature, and establishing a heating interval start time at a time prior to the idle end point generally at a time sufficient to provide the determined necessary heating interval time period.

14. The vehicle fluid heating system of claim 1 wherein the controller is in communication with the temperature sensor for receiving temperature information, the controller being configured to only permit electricity to flow from the electrical source to the first and second vehicle fluid heaters when the temperature information received from the temperature sensor indicates that the temperature of the temperature source is below a predetermined turn-on set temperature, and is configured to not permit electricity to flow from the electrical source to the first and second vehicle fluid heaters if the temperature information indicates that the temperature of the temperature source is above a predetermined turn-offset temperature.

15. The vehicle fluid heating system of claim 14 wherein the turn-on set temperature is between about ten and twenty degrees lower than the turn-offset temperature.

16. The vehicle fluid heating system of claim 1 wherein the controller is configured for providing a time interval between the actuator of the switch for allowing electricity to flow to the first vehicle fluid heater and the actuation of the switch for allowing electricity to flow to the second vehicle fluid heater.

17. The vehicle fluid heating system of claim 1 further comprising an input device for enabling the user to input operational instructions into the controller including idle period start point and end point data and override data for altering the system devices on idle period.

18. The vehicle fluid heating system of claim 1 wherein the controller comprises a programmable logic controller capable of separately and independently controlling at least a first, second, third and fourth vehicle fluid heater.

19. The vehicle fluid heating system of claim 18 wherein the first, second, third and fourth vehicle fluid heaters comprise a plurality of first, second, third and fourth vehicle fluid heaters.

* * * * *